US009862957B2

(12) United States Patent
Thevelein et al.

(10) Patent No.: US 9,862,957 B2
(45) Date of Patent: Jan. 9, 2018

(54) SPECIFIC ALLELES IMPORTANT FOR ETHANOL TOLERANCE

(71) Applicants: VIB VZW, Ghent (BE); Katholieke Universiteit Leuven, K.U.Leuven R&D, Leuven (BE)

(72) Inventors: Johan Thevelein, Blanden (BE); Maria Remedios Foulquie-Moreno, Brussels (BE); Annelies Goovaerts, Putte (BE); Steve Swinnen, Zichem (BE)

(73) Assignees: VIB VZW, Ghent (BE); KATHOLIEKE UNIVERSITEIT LEUVEN, K. U. LEUVEN R&D, Leuven (BE)

( * ) Notice: Subject to any disclaimer, the term of this patent is extended or adjusted under 35 U.S.C. 154(b) by 0 days.

(21) Appl. No.: 15/200,542

(22) Filed: Jul. 1, 2016

(65) Prior Publication Data

US 2016/0304888 A1   Oct. 20, 2016

Related U.S. Application Data

(63) Continuation of application No. 14/129,073, filed as application No. PCT/EP2012/061823 on Jun. 20, 2012, now abandoned.

(30) Foreign Application Priority Data

Jun. 21, 2011 (EP) .................... 11170692

(51) Int. Cl.
  *C12N 15/81* (2006.01)
  *C12Q 1/02* (2006.01)
  *C12Q 1/68* (2006.01)
  *C12P 7/06* (2006.01)

(52) U.S. Cl.
  CPC ........... *C12N 15/81* (2013.01); *C12N 15/815* (2013.01); *C12P 7/06* (2013.01); *C12Q 1/025* (2013.01); *C12Q 1/6895* (2013.01); *C12Q 2600/156* (2013.01); *Y02E 50/17* (2013.01)

(58) Field of Classification Search
  None
  See application file for complete search history.

(56) References Cited

U.S. PATENT DOCUMENTS

2014/0228224 A1   8/2014   Thevelein et al.

FOREIGN PATENT DOCUMENTS

| WO | 03062430   | 7/2003  |
| WO | 2009029644 | 3/2009  |
| WO | 2012175552 | 12/2012 |

OTHER PUBLICATIONS

Hong, M., et al., "Identification of gene targets eliciting improved alcohol tolerance in *Saccharomyces cerevisiae* through inverse metabolic engineering," Journal of Biotechnology 149 (2010) 52-59.
Swinnen, S., et al., "Identification of novel causative genes determining the complex trait of high ethanol tolerance in yeast using pooled-segregant whole-genome sequence analysis," Genome Research 22: 975-984, May 2012.
Wei, W., et al., "Genome sequencing and comparative analysis of *Saccharomyces cerevisiae* strain YJM789," Proceedings of the National Academy of Sciences, vol. 104, No. 31, pp. 12825-12830, Jul. 2007.
International Search Report and Written Opinion for International Application No. PCT/EP2012/061823, dated Sep. 4, 2012, 12 pages.
Yang (Biotechnology and Bioengineering vol. 108 No. 8 Aug. 2011 (pre-published online Mar. 17, 2011)).
Deutschbauer et al., Quantitative trait loci mapped to single-nucleotide resolution in yeast, Nature Genetics, 2005, vol. 37, No. 12.

*Primary Examiner* — Paul J Holland
(74) *Attorney, Agent, or Firm* — TraskBritt, P.C.

(57) ABSTRACT

The present disclosure relates to the identification of a QTL associated with high ethanol tolerance in *Saccharomyces* spp. More specifically, it relates to specific alleles of MKT1 and APJ1 possibly combined with a specific allele of SWS2 that are important in obtaining a high ethanol tolerance in *Saccharomyces* spp. It relates further to the use of such alleles in the construction of high ethanol tolerant strains, and the use of these alleles in screening for ethanol tolerance.

20 Claims, 13 Drawing Sheets
(3 of 13 Drawing Sheet(s) Filed in Color)

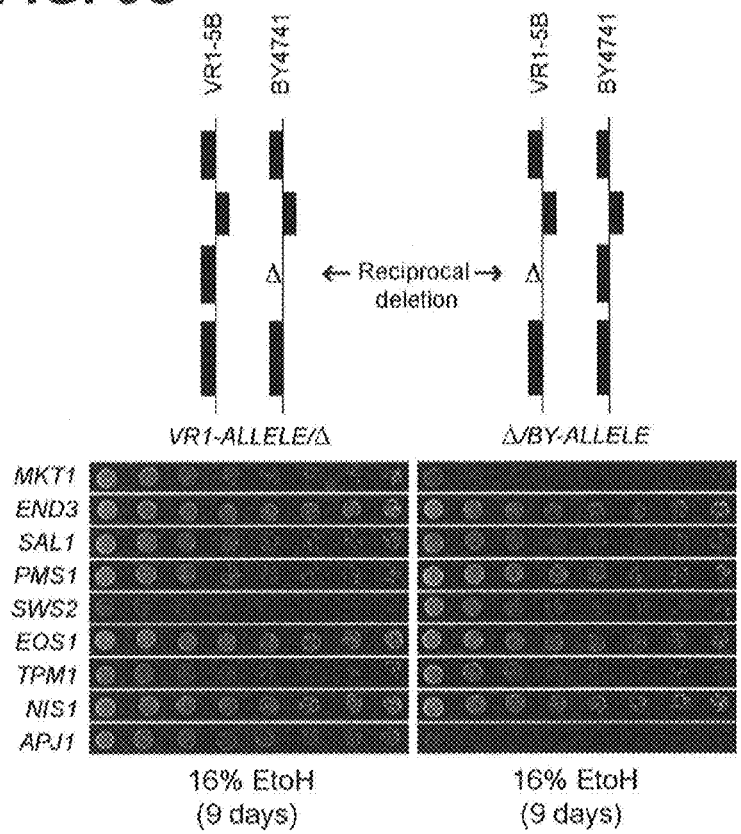

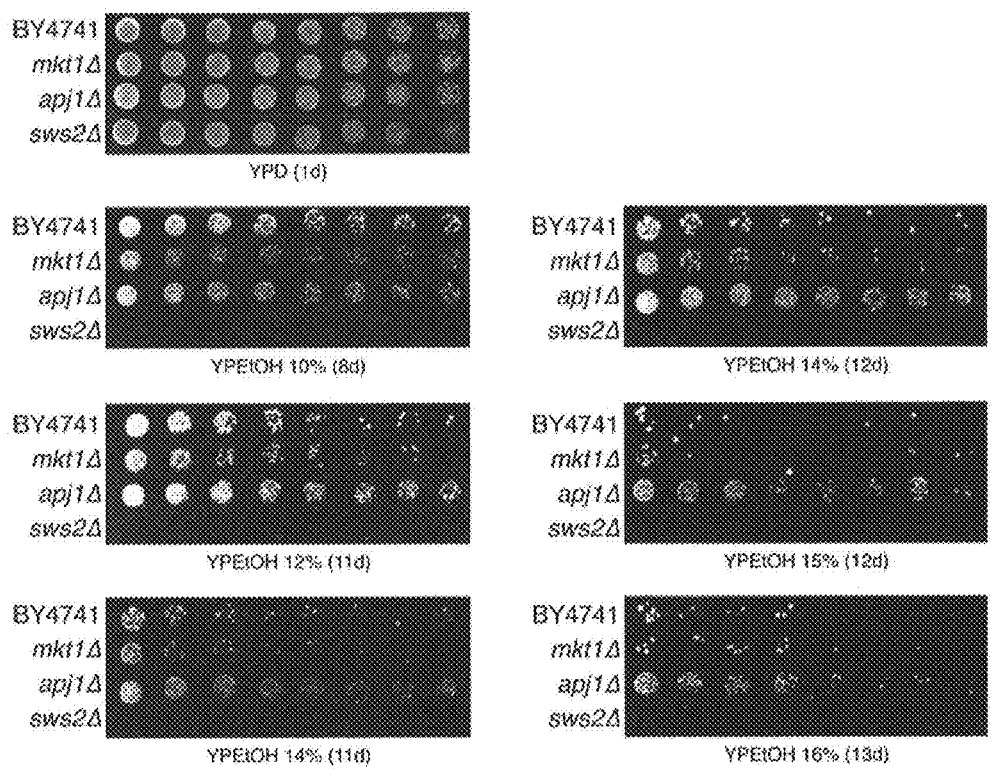

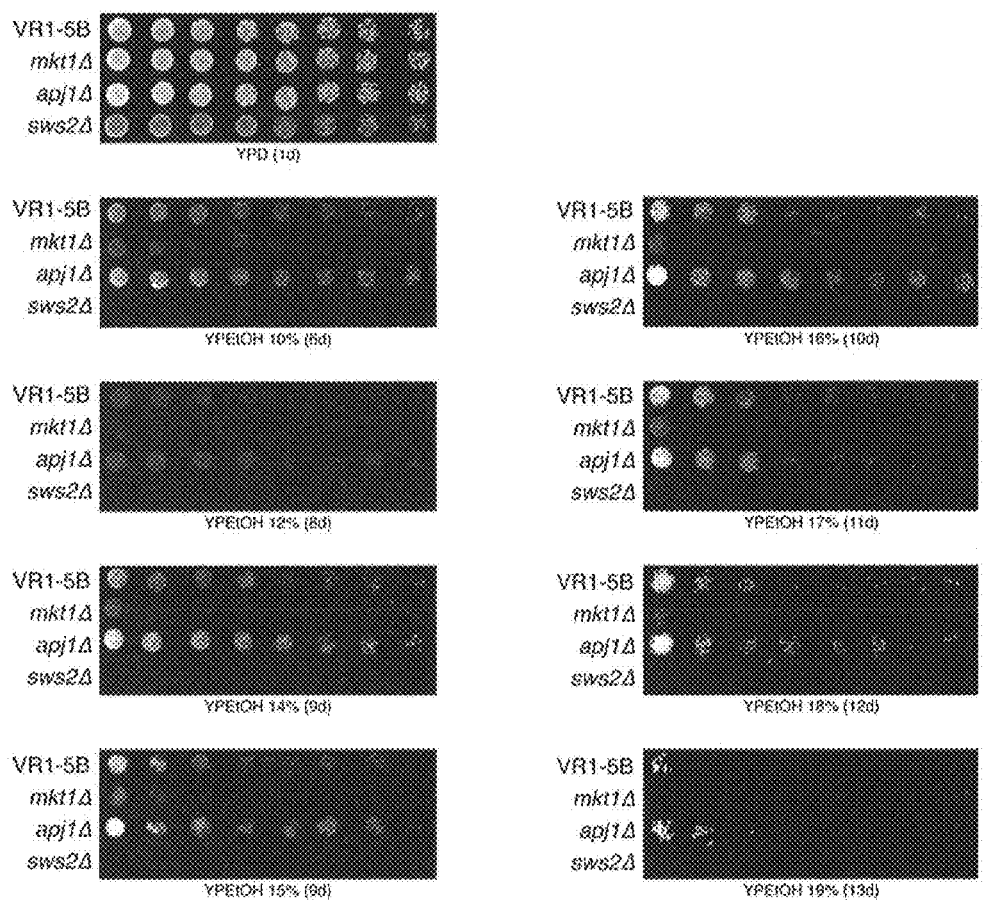

US 9,862,957 B2

SPECIFIC ALLELES IMPORTANT FOR ETHANOL TOLERANCE

CROSS-REFERENCE TO RELATED APPLICATIONS

This application is a continuation of U.S. patent application Ser. No. 14/129,073, filed Apr. 23, 2014, pending, which is a national phase entry under 35 U.S.C. §371 of International Patent Application PCT/EP2012/061823, filed Jun. 20, 2012, designating the United States of America and published in English as International Patent Publication WO 2012/175552 A1 on Dec. 27, 2012, which claims the benefit under Article 8 of the Patent Cooperation Treaty to European Application Serial No. 11170692.5, filed Jun. 21, 2011, the disclosure of each of which is hereby incorporated herein in its entirety by this reference.

TECHNICAL FIELD

The present disclosure relates to the identification of a QTL associated with high ethanol tolerance in *Saccharomyces* spp. More specifically, it relates to specific alleles of MKT1 and APJ1 possibly combined with a specific allele of SWS2 that are important in obtaining a high ethanol tolerance in *Saccharomyces* spp. It relates further to the use of such alleles in the construction of high ethanol tolerant strains, and the use of these alleles in screening for ethanol tolerance.

BACKGROUND

Genetic analysis of polygenic, quantitative traits remains an important challenge. It requires reliable scoring of many genetic markers covering the whole genome. In yeast, the first successful approaches to simultaneously map multiple genetic loci, that were either independent (Winzeler et al., 1998) or involved in a quantitative trait (QTL) Steinmetz et al., 2002), made use of SNP markers that were scored by hybridization of genomic DNA from individual segregants to a gene expression micro-array. Subsequently, a similar approach was used to map QTL involved in traits such as sporulation efficiency (Deutschbauer and Davies, 2005), gene expression (Brem et al., 2002), acetic acid production (Marullo et al., 2007), cell morphology (Nogami et al., 2007) and resistance to small-molecule drugs (Perlstein et al., 2007).

The advent of high-throughput sequencing technologies provides a new way to score large numbers of SNPs as genetic markers. Application to individual segregants remains cumbersome because of the high costs involved. On the other hand, bulked segregant analysis was shown to be efficient in identifying markers linked to specific genes (Michelmore et al., 1991) and is robust to occasional phenotyping mistakes (Segré et al., 2006). Schneeberger et al., (2009) showed that this approach worked for a single mutation. They crossed an *Arabidopsis thaliana* mutant with an unrelated strain, pooled 500 segregants with the mutant phenotype and used the nucleotide frequency of SNPs detected by Illumina whole genome sequence analysis in the DNA extracted from the pool to map the locus with the mutation. Recently, Arnold et al., (2011) used a similar approach to identify a single mutation responsible for a renal disease in mice and Birkeland et al., (2010) to map a mutation causing a defect in vacuole inheritance in *S. cerevisiae*. It has been suggested that in principle this approach should also allow the simultaneous mapping of multiple QTL present throughout the genome (Schneeberger et al., 2009; Birkeland et al., 2010; Lister et al., 2009). However, to the best of our knowledge, this has not been demonstrated yet for a typical quantitative trait.

BRIEF SUMMARY

For this disclosure, we applied "pooled-segregant whole genome sequence analysis" for the mapping of QTL involved in tolerance to high ethanol levels (16-17%) in yeast. High ethanol tolerance is an exquisite characteristic of the yeast *Saccharomyces cerevisiae* and is of prime importance to the yeast fermentation industries (bioethanol, beer, wine and other alcoholic beverages). Up to now, ethanol tolerance in yeast has been studied mostly in laboratory yeast strains and always with low to moderately high ethanol concentrations (5-12%). These studies have revealed that properties like membrane lipid composition, chaperone protein expression, and trehalose content are important determinants of ethanol tolerance (D'Amore and Stewart, 1987; Ding et al., 2009). Genome-wide transcriptomics and screening of deletion mutants have revealed many genes required for tolerance to low/moderate ethanol concentrations Fujita et al., 2006; Lewis et al., 2010; van Voorst et al., 2006). In most of these studies, ethanol tolerance was determined based on growth in the presence of ethanol. Furthermore, a genetic dissection of ethanol tolerance was made in laboratory strains in which ethanol tolerance was measured as survival after treatment with different concentrations of ethanol under non-growing conditions. Short Tandem Repeats (STRs) and Single Nucleotide Polymorphisms (SNPs), detected by multiplex PCR, were used as genome-wide genetic markers and five QTL were identified which explained about 50% of the phenotypic variation (Hu et al., 2007). In contrast, nothing is known about the genetic loci or gene polymorphisms that are responsible for the much higher ethanol tolerance during growth of natural and industrial yeast strains compared to laboratory strains.

Surprisingly, we found that "pooled-segregant whole genome sequence analysis" can be used for mapping of QTL in yeast. Even more surprisingly, we have identified and validated three genetic loci in a Brazilian bioethanol production strain that are responsible for tolerance to high ethanol levels during growth. In addition, we have dissected the locus with the strongest linkage and identified two novel alleles with a previously unrecognized, positive function in ethanol tolerance. The locus also contained a mutant allele with a negative contribution to high ethanol tolerance, which was located in between the two genes with a positive contribution.

A first aspect of the disclosure is the use of an inactivated APJ1 (SEQ ID NO:2, accession number: genbank NP_014322 version NP_014322.1, 26 Apr. 2011) allele, or a homologue, orthologue or paralogue thereof, to obtain ethanol tolerance in yeast. Inactivated, as used here, means that the expression can be lowered by mutations in the promoter region, or that mutants in the open reading frame may occur, affecting the biological activity of the gene. A "homologue," as used here, encompasses a gene encoding a protein having amino acid substitutions, deletions and/or insertions relative to the unmodified protein in question and having similar biological and functional activity as the unmodified protein from which it is derived. "Orthologue" and "paralogue" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene. Preferably, the homologue, orthologue or paralogue shows at least 40% identities at protein level, as measured by a BLASTp alignment (Altschul et al., 1997; Altschul et al., 2005). Even more preferably, it has at least 45%, more preferably 50%, more preferably 55%, more preferably 60%, more preferably 65%, more preferably 70%, more preferably 75%, more preferably 80%, more preferably 85%, more preferably 90%, most preferably 95% identities. Preferably, the inactivated allele is a disrupted or deleted APJ1 mutant, including the complete deletion of the gene. The use of an inactivated allele, as used here, means that in a haploid strain the APJ1 gene is replaced by the inactivated allele, and in a diploid or polyploidy or aneuploid yeast strain, at least one copy of the APJ1 gene is replaced by the inactivated allele. Preferably, several copies are replaced; most preferably all copies are replaced by the inactivated allele. Ethanol tolerance, as used here, means that the strain, carrying the inactivated allele can be grown at higher ethanol concentrations than the parental strain. Preferably, ethanol tolerance means that the stain is capable to grow on plates with at least 12% ethanol, preferably on plates with at least 14% ethanol, more preferably on plates with at least 16%, more preferably at least 17%, most preferably at least 18% ethanol. A "yeast," as used here, can be any unicellular fungus. Preferably, the yeast is a species selected from the genera *Saccharomyces, Zygosaccharomyces, Brettanomyces, Kluyveromyces, Pichia, Pachysolen* and *Candida*. Preferably, the yeast is a brewers', wine or distillers yeast selected from the genera *Saccharomyces, Zygosaccharomyces* and *Brettanomyces*. Most preferably, the yeast is a *Saccharomyces* spp, preferably *Saccharomyces cerevisiae*.

In one preferred embodiment, the use of the inactivated APJ1 allele is combined with the use of a mutant MKT1 allele. The use of a mutant MKT1 allele, as used here, means that in a haploid strain the MKT1 gene is replaced by the mutant allele, and in a diploid or polyploidy or aneuploid yeast strain, at least one copy of the MKT1 gene is replaced by the mutant allele. Preferably, several copies are replaced; most preferably all copies are replaced by the mutant. A mutant MKT1 gene is a gene that encodes a protein that is different from the reference protein (SEQ ID NO:3, Genbank accession number CAA95961, version CAA95961.1 dated 11 Aug. 1997). Preferably, the mutant encodes a protein carrying mutation at positions 30 and 453, more preferably, the mutant encodes a protein that has a glycine at position 30 and an arginine at position 453, most preferably, the mutant encodes a protein that comprises, preferably consists of SEQ ID NO:1 (table 3). Alternatively, the mutant MKT1 allele is a mutant of a homologue, orthologue of paralogue (as defined earlier) of the gene encoding MKT1.

In another preferred embodiment, the use of the inactivated APJ1 allele is combined with the overexpression of a wild type SWS2 gene. A wild type SWS2 gene is a gene encoding a sws2p as given by SEQ ID NO:4 (Genbank accession number NP_014318, version NP_014318.1 dated 26 Apr. 2011) or a homologue, orthologue or paralogue thereof, as defined above. Overexpression, as used here, means that the level of SWS2 protein in the strain carrying the inactivated APJ1 is higher than in the parental strain. As a non-limiting example, overexpression can be obtained by placing the coding sequence under control of a strong promoter, or by increasing the copy number of the gene.

It is clear for the person skilled in the art that the inactivated APJ1 allele can be combined with both overexpression of the wild type SWS2 gene, as well as the expression of a mutant MKT1 allele, according to the disclosure. Moreover, other ethanol tolerance improving genes can be used to increase the effect of the inactivated APJ1 allele, whether in combination with wild type SWS2 and/or mutant MKT1 or not.

Alternatively, the expression of mutant MKT1 allele, according to the disclosure, or overexpression of the wild type SWS2 gene may be used alone to obtain ethanol tolerance, or the combination of the expression of mutant MKT1 allele, according to the disclosure, with overexpression of the wild type SWS2 gene can be used to obtain ethanol tolerance.

Another aspect of the disclosure is a method for screening ethanol resistant yeast, the method comprising the identification of downregulating mutations in the APJ1 gene and/or the determination of the G30 and/or R453 mutation in the Mkt1p. The APJ1 gene, as used here, includes the promoter and terminator region. Downregulating mutations are known to the person skilled in the art and include, but are not limited to, insertions, deletions of premature stops in the coding sequence. Determination of G30 and/or R453 mutation in the Mkt1p can be carried out at protein level or at nucleic acid level; preferably, it is carried out at nucleic level, by checking the coding sequence.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A: QTL mapping by whole-genome sequence analysis of DNA extracted from a pool of 136 segregants tolerant to at least 16% ethanol (Pool 1). The genomic DNA of the parents, VR1-5B and BY4741, and the pool was sequenced and aligned to identify SNPs. The nucleotide frequency of quality-selected SNPs in the sequence of the pool was plotted against the chromosomal position. Significant deviations from the average of 0.5 indicate candidate QTL linked to high ethanol tolerance. Upward deviations indicate linkage to QTL in the ethanol tolerant parent VR1-5B.

FIG. 2B: Application of a more stringent selection condition reveals candidate minor loci determining high ethanol tolerance. For a locus on chromosome II and XV, the SNP frequencies in the pool of segregants tolerant to at least 17% ethanol (red line) show a more pronounced deviation from random segregation in comparison to the pool of segregants tolerant to at least 16% ethanol (green line). The difference in SNP frequency between the two pools is certainly significant when the confidence intervals do not overlap.

FIGS. 6A-6C: Fine-mapping and identification of the causative genes in QTL3.

FIG. 6A: The 87 kb locus defined by SNP markers S67, S68 and S69 in QTL3 showed the lowest probability of random segregation in 101 highly ethanol tolerant segregants. Further fine-mapping was achieved by scoring five additional markers within the 87 kb interval in the same segregants. Calculation of the P values revealed the strongest link for a 16 kb locus defined by markers S68, S68-1 and S68-2.

FIG. 6B: The name and location of each ORF in the fine-mapped locus is shown as annotated in SGD 20. The interval from nucleotide 466,599 till 485,809 was sequenced in VR1-5B and BY4741, which revealed 115 polymorphisms, of which part were in intergenic regions (numbers between brackets). For the ORFs, only polymorphisms that change the amino acid sequence are indicated (amino acid in BY4741, followed by position in the protein and amino acid in VR1-5B). SAL1 has a frame shift mutation in BY4741 resulting in an earlier stop codon and truncation of the protein, which is assumed to be a loss-of-function gene product (Dimitrov et al., 2009). PMS1 has an insertion of four amino acids at position 417 in VR1-5B. The sequence of BY4741 in this interval is the same as that of S288c 20, except for one nucleotide in SAL1 that causes an amino acid change at position 131 (valine in BY4741 and methionine in S288c and VR1-5B).

FIG. 6C: Reciprocal hemizygosity analysis. For each gene in the fine-mapped locus, two diploid strains were constructed in the VR1-5B/BY4741 hybrid background that carried either the VR1-5B-derived (left) or BY4741-derived (right) allele from the gene. The rest of the genome was identical between the two hybrids. The reciprocal deletions were engineered in the haploid strains, after which the proper haploids were crossed to obtain the diploid hybrids. The ethanol tolerance of the diploid hybrids was determined by scoring the growth of twofold dilutions on 16% ethanol after 9 days. This revealed different contributions of the parental alleles of MKT1, SWS2 and APJ1 to high ethanol tolerance.

FIGS. 7A-7C: Effect of MKT1, SWS2 and APJ1 on ethanol tolerance.

FIG. 7A: The ethanol tolerance of BY4741 (inferior wild type) and its MKT1, SWS2 and APJ1 deletion strains was determined by scoring growth of twofold dilutions on different ethanol concentrations.

FIG. 7B: The ethanol tolerance of VR1-5B (superior wild type) and its MKT1, SWS2 and APJ1 deletion strains was determined by scoring growth of twofold dilutions on different ethanol concentrations.

FIG. 7C: The MKT1-VR allele is beneficial for high ethanol tolerance. MKT1-BY and MKT1-VR including 534 bp upstream and 344 bp downstream regions of the ORF were cloned in the low-copy-number plasmid YCplac111 and expressed in BY4741 (BY1) and three segregants from VR1-5B/BY4741 that hold MKT1-BY (1D, 24A and 32B). The ethanol tolerance was determined in two-fold dilutions on different concentrations of ethanol.

FIG. 11A: Fermentation profile measured from weight loss due to CO2 release. FIG. 11B: Final ethanol level. FIG. 11C: Final glucose leftover, and ethanol and glycerol produced. The stirred fermentation has no indication, the static fermentation is indicated as (static). GS1.11-26 is the parental strain, the double mutant is indicated as GS1.11-26 APJ1 ΔΔ.

EXAMPLES

Figure 1:
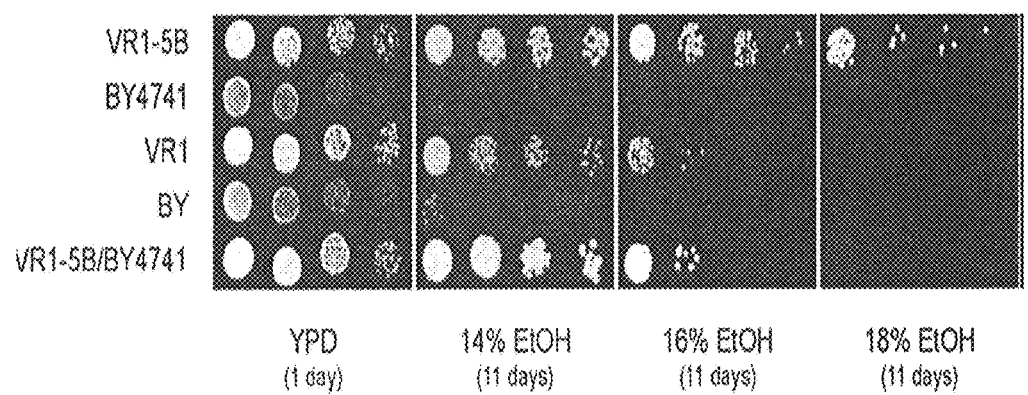
FIG. 1: Ethanol tolerance of the Brazilian bioethanol production strain VR1 and its segregant VR1-5B. The ethanol tolerance of VR1 (diploid) and VR1-5B (haploid) was determined by scoring growth of tenfold dilutions on YP plates with different concentrations of ethanol. Both strains, as well as the heterozygous VR1-5B/BY4741 strain (diploid), showed a clearly higher ethanol tolerance than the control laboratory strains BY4741 (haploid) and BY (diploid), which was obtained by crossing BY4741 with BY4742.

Materials and Methods to the Examples
Strains and Growth Conditions
Yeast cells were grown at 30° C. in YPD medium containing 1% (w/v) yeast extract, 2% (w/v) Bacto peptone and 2% (w/v) glucose. Selection of transformants was done with 100 μg/ml geneticin. Selection for amino acid prototrophy was performed in minimal media containing complete supplement mixture without the amino acid under study, 0.17% (w/v) yeast nitrogen base without amino acids and ammonium sulphate, 0.5% (w/v) ammonium sulphate and 2% (w/v) glucose (pH 5.5). For solid plates, 1.5% (w/v) Bacto agar was added and the pH was adjusted to 6.5.

E. coli cells (TOP10; genotype F-mcrA Δ(mrr-hsdRMS-mcrBC) φ80lacZΔM15 ΔlacX74 recA1 araD139 Δ(ara leu) 7697 galU galK rpsL (StrR) endA1 nupG) were grown at 37° C. in luria broth (LB) medium containing 0.5% (w/v) yeast extract, 1% (w/v) Bacto tryptone and 1% (w/v) sodium chloride (pH 7.5). For solid plates, 1.5% (w/v) Bacto agar was added and the pH was adjusted to 6.5. Selection of transformants was done with 100 μg/ml ampicillin.

The yeast strains BY4741 (MATa his3Δ1 leu2Δ0 met15Δ0 ura3Δ0), BY4742 (MATα his3Δ1 leu2Δ0 lys2Δ0 ura3Δ0) and S288c (MATα) have been described by Brachmann et al., (1998). VR1 is a natural isolate and former production strain in Brazilian bio-ethanol with sugar cane (Fermenter, Piracicaba, Brazil). VR1-5B is a haploid (MATα) segregant of VR1, with similarly high ethanol resistance. Ethanol Red is a commercial bio-ethanol productions strain (Lesaffre)

ES2 and PE2 are bioethanol productions strains from AB Mauri (Australia) and Fermentec (Brazil), respectively. GS1.11-26 is a xylose fermenting derivative of the Ethanol Red strain.

General Molecular Biology Methods

Genomic DNA was extracted from yeast according to Hoffman and Winston (1987). When required, additional purification was performed by ethanol precipitation. Polymerase chain reaction (PCR) was performed with Accuprime (Invitrogen) for cloning and sequencing purposes and with ExTaq (TAKARA) for diagnostic purposes. Yeast was transformed with the LiAc/PEG method (Gietz et al., 1995). Cloning was performed by standard techniques. Dephosphorylation was performed with rAPid Alkaline Phosphatase (Roche) and ligation with T4 DNA ligase (Roche). E. coli was transformed with the CaCl2 method (Sambrooke et al., 1989) and plasmid DNA isolated according to Del Sal et al., (1988).

Plasmid YCplac111 was described by Gietz and Sugino (1988). YCplac111(MKT1-BY) and YCplac111(MKT1-VR) are the YCplac111 derivatives carrying the MKT1 gene from BY4741 and VR-5B, respectively, pFA6-kanMX4 was described by Wach et al., (1994)

Mating, Sporulation and Tetrad Analysis

Mating, sporulation and tetrad analysis were performed by standard procedures (Sherman and Hocks, 1991). The mating type of the segregants was determined by diagnostic PCR for the MAT locus (Huxley et al., 1990).

Ethanol Tolerance Test

Strains were inoculated in YPD and grown at 30° C. for 3 days till stationary phase. Cultures were diluted to an OD600 of 0.5 and 5 μl of a twofold (100 till 8.10-3) or tenfold (100 till 10-3) dilution range was spotted on YPD and YP with different concentrations of ethanol. Growth was scored after one day for control YPD plates and 9 to 11 days for plates with ethanol. All spot tests were repeated at least twice starting from independent cultures.

High Gravity Fermentations

Small scale fermentation was performed in 100 ml YP+35% (w/v) glucose. Strains were first pre-grown in 5 ml YPD medium for about 24 hours at 30° C. The pre-culture was then transferred to 60 ml YPD medium at an initial OD600 of 1. After the cells were allowed to grow to stationary phase, they were harvested by centrifugation at 3000 rpm at 4° C. for 3 minutes, and the pellet was inoculated into 100 ml fermentation medium. For stirring fermentation, continuous stirring was applied at 120 rpm. For static fermentation, the cells were agitated only for the first 4 hours. The glucose leftover was calculated from the weight loss measurement resulted from $CO_2$ evolution. Samples were taken at the end of the fermentation and analyzed for the glucose leftover, produced ethanol and glycerol by HPLC.

Genotyping of SNP Markers by PCR

For each SNP marker, two primers were constructed that differed only at their 3' terminal end nucleotide. In particular, one primer contained the VR1-5B nucleotide, while the other primer contained the BY4741 nucleotide. Both primers were always applied in separate PCR reactions with a common indirect primer. The two primer pairs were investigated for their ability to specifically amplify the VR1-5B or BY4741 sequence by performing four PCR reactions at different hybridization temperatures that differed in the combination of DNA and primer pairs. The combinations were: (1) DNA from BY4741 with primer pair for BY4741, (2) DNA from BY4741 with primer pair for VR1-5B, (3) DNA from VR1-5B with primer pair for BY4741 and (4) DNA from VR1-5B with primer pair for VR1-5B. The PCR reactions were performed at hybridization temperatures from 58° C. till 66° C. (2° C. increments). The hybridization temperature at which the VR1-5B and BY4741 sequences were specifically amplified was subsequently applied to genotype the SNP marker in individual highly ethanol tolerant segregants. Each SNP marker check included VR1-5B and BY4741 as controls.

Real-Time PCR

For measurement of APJ1 expression, samples were taken from early exponential-phase grown cells of BY4741 and VR1-5Ba. Pellets were frozen in liquid nitrogen and stored at −80° C. RNA extraction was performed using the phenol chloroform method. cDNA was prepared following the instructions of the GoScript™ Reverse Transcription System kit (Promega). Relative quantification of APJ1 and 18S was performed using a StepOnePlus Real-time PCR system (Applied Biosystems), primers: Fw APJ1 (TGATGGGCACGGTGGTCTA) (SEQ ID NO:5), Rv APJ1 (TTGAATACCTTGCCCTTTGCA) (SEQ ID NO:6), Fw 18S (CACTTCTTAGAGGGACTATCGGTTTC) (SEQ ID NO:7) and Rv 18S (CAGAAC GTCTAAGGGCATCACA) (SEQ ID NO:8).

Preparation of DNA Samples for Whole-Genome Sequencing

The two parent strains VR1-5B and BY4741 and all segregants with high ethanol tolerance were grown individually in 50 ml YPD at 30° C. for 3 days. Exactly 10 ml of each culture was filtered, after which the cells were dried in the microwave and weighed to establish the relationship between optical density and dry weight. The remaining culture volumes were stored at −80° C. The two pools of segregants were constructed by combining equal amounts of cells from the stored cultures based on dry weight. The genomic DNA from the parent strains and the pools was extracted according to Johnston (1994). At least 3 μg of each DNA sample was provided to GATC Biotech AG (Konstanz, Germany) for sequencing.

Reciprocal Hemizygosity Analysis

All deletions for reciprocal hemizygosity analysis were made in the haploid backgrounds. The BY4741 deletion strains were obtained from the deletion strain collection (Giaever et al., 2002). The deletions in the VR1-5B background were made using the same primers and strategy as the International Deletion Consortium (Giaever et al., 2002; Winzeler et al., 1999). The transformants were selected on geneticin plates and verified by PCR with several combinations of internal and external primers. The haploid strains were subsequently crossed to construct the diploid hybrid strains. The presence of both the wild type and deletion allele of the gene in the diploid hybrids was verified by PCR. The reciprocal hemizygosity analysis was performed twice starting from independent PCR amplifications and transformations.

Statistical Analysis

For every chromosome, the quantified frequencies of the detected SNPs were considered to be binomially distributed. The underlying structure in the SNP scatterplot of a given chromosome (FIGS. 2A and 2B) was identified by fitting smoothing splines in the generalized linear mixed model framework 48. The number of knots of the spline was chosen such that they are spaced at approximately 40 kb intervals. Simultaneous confidence bands 48 for the fitted smoother were constructed and allowed identification of regions that are significantly different from a baseline, i.e., a SNP frequency of 50%. For chromosome II and XV, the data from both pools of segregants (16% and 17% ethanol) were simultaneously modeled with generalized additive mixed models with a smoother for the mean trend (FIG. 2B) and for the difference between both pools. For graphical representation we have chosen to represent the resulting fit for each pool and their simultaneous confidence bands. The difference in SNP frequency between the two pools is certainly significant when the simultaneous confidence bands do not overlap.

Example 1: Characterization of Parent Strains with High and Low Ethanol Tolerance A segregant called VR1-5B was isolated from the Brazilian bioethanol production strain VR1 that displayed similarly high ethanol tolerance as the parent strain. Ethanol tolerance was thereby defined as growth on solid YP plates with ethanol as the sole carbon source. Because high ethanol tolerance is only relevant towards the end of yeast fermentation when the sugar level has dropped to low values, ethanol tolerance was determined in the absence of any other sugar or carbon source. The VR1 parent strain could grow in medium containing up to 16% ethanol, while the VR1-5B segregant showed growth in medium containing up to 18% ethanol (FIG. 1). Both strains were clearly more ethanol tolerant than the control haploid BY4741 and diploid BY laboratory strains, which could grow only slightly in medium with 14% ethanol (FIG. 1). The diploid VR1-5B/BY4741 strain displayed similarly high ethanol tolerance to the VR1 parent strain, indicating that the high ethanol tolerance in this strain is a dominant property (FIG. 1).

Example 2: Pooled-Segregant Whole Genome Sequence Analysis

Figure 2A:
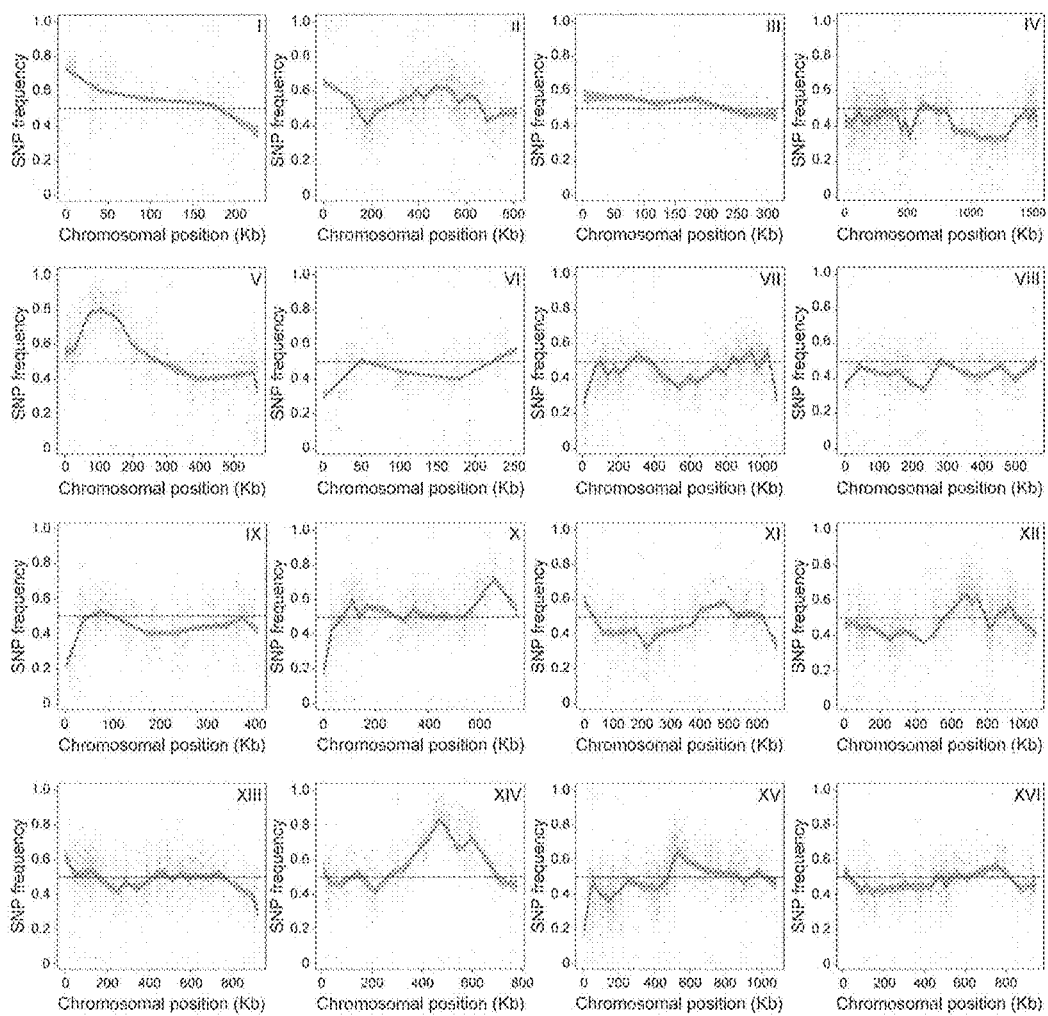
FIGS. 2A and 2B: Genetic mapping of QTL involved in high ethanol tolerance by whole genome sequence analysis.

From the cross between VR1-5B and BY4741, we obtained 5974 segregants that were phenotyped for ethanol tolerance by scoring growth on YP with different concentrations of ethanol. The segregants with extreme phenotypes were subsequently classified in two pools. The first pool contained 136 segregants with a tolerance to at least 16% ethanol (Pool 1) and the second pool contained 31 segregants from the first pool with a tolerance to at least 17% ethanol (Pool 2). All segregants were individually grown up till stationary phase, after which equal amounts of cells based on dry weight were combined to obtain Pool 1 and Pool 2. The genomic DNA from both pools and the parent strains was extracted and submitted to custom sequence analysis using Illumina HiSeq 2000 technology (GATC Biotech AG, Konstanz, Germany). The sequencing was performed at 40 times or greater coverage and generated paired-end short reads of about 100 bp allowing a highly precise alignment of the reads. The VR1-5B and BY4741 sequences were aligned to the reference S288c genome sequence 20 and SNPs between VR1-5B and BY4741 with a coverage of more than 20 times and a ratio of at least 80% were selected. Subsequently, the sequence of the pool was aligned to the BY4741 sequence and the nucleotide frequency of each SNP was plotted against its chromosomal position. The SNP nucleotide frequency curve obtained by whole-genome sequencing of DNA extracted from Pool 1 (16% ethanol) fluctuated around 50% in most areas in the genome (FIG. 2A).

Figure 2B:
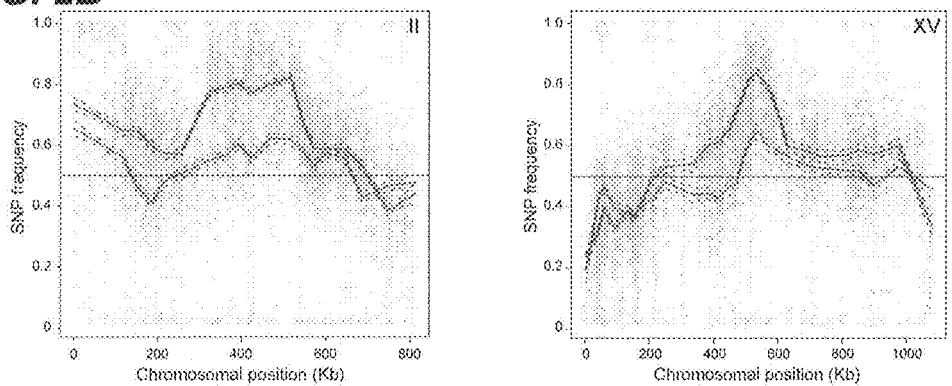
Figure 3:
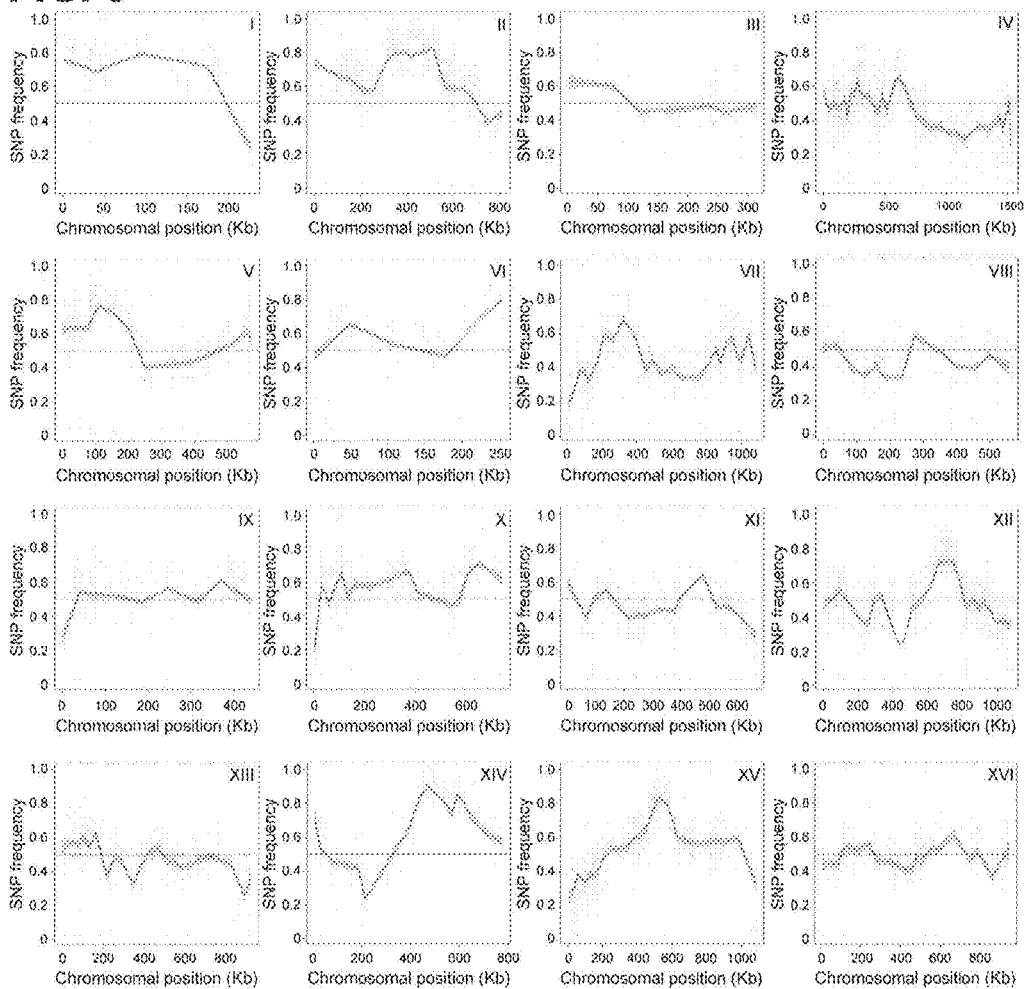
FIG. 3: Genetic mapping by whole-genome sequence analysis of DNA extracted from a pool of 31 segregants tolerant to at least 17% ethanol (Pool 2). The genomic DNA of the parents, VR1-5B and BY4741, and the pool was sequenced and aligned to identify SNPs. The nucleotide frequency of quality-selected SNPs in the sequence of the pool was plotted against the chromosomal position. Significant deviations from the average of 0.5 indicate candidate QTL linked to high ethanol tolerance. Upward deviations indicate linkage to QTL in the ethanol tolerant parent VR1-5B.
Figure 4:
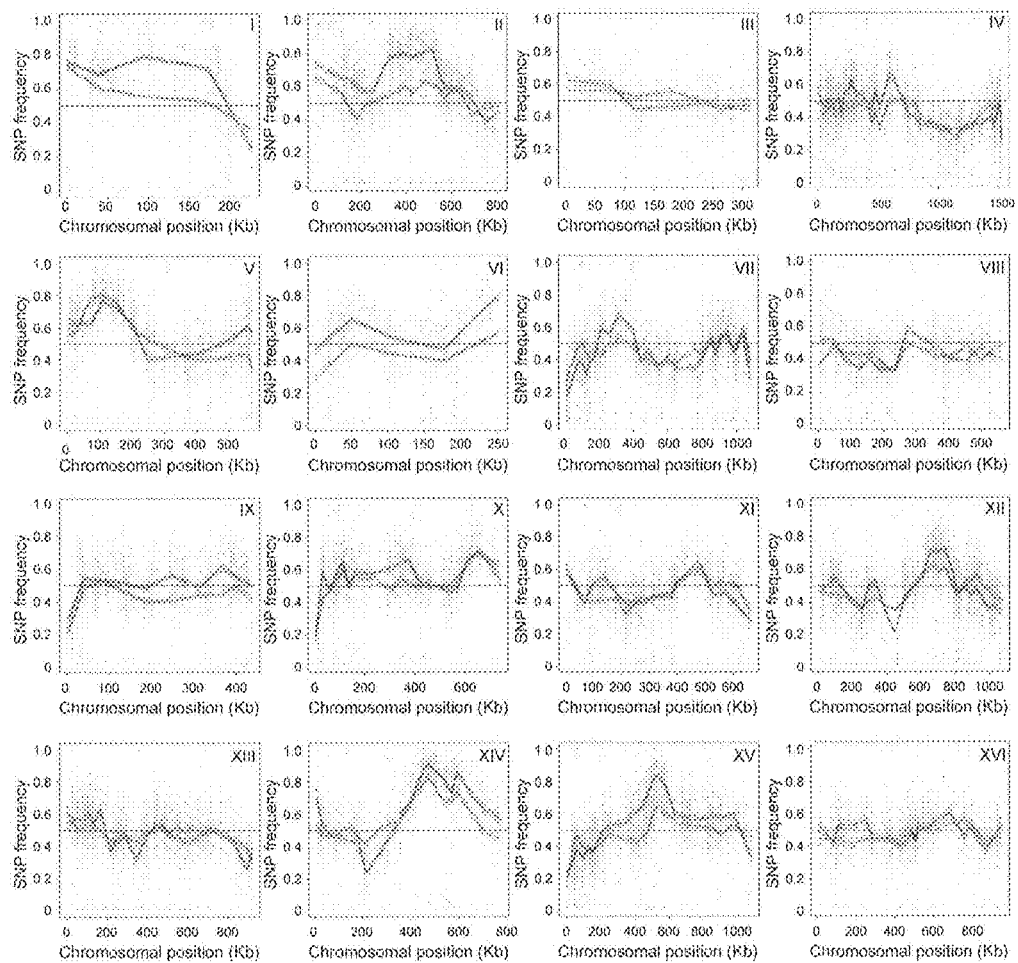
FIG. 4: Comparison of the evolution of the SNP nucleotide frequency for Pool 1: segregants tolerant to 16% ethanol (green line) and Pool 2: segregants tolerant to 17% ethanol (red line) throughout the genome. The two major QTL on chromosomes V and XIV are not significantly different between the two pools. However, in several instances, e.g., on chromosomes II, XII and XV, minor loci can be identified showing a significant difference between the two pools. These candidate QTL are more distinctive in Pool 2 (17% ethanol) compared to Pool 1 (16% ethanol). The difference in SNP frequency between the two pools is certainly significant when the simultaneous confidence bands do not overlap.
Figure 5A:
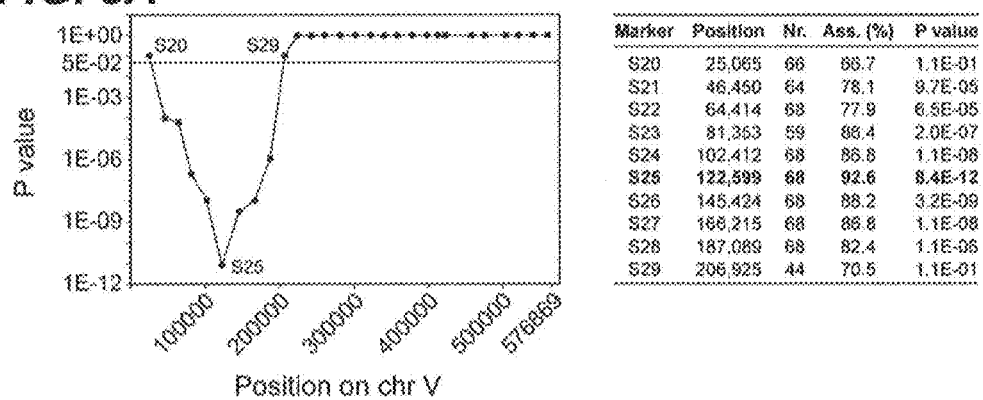
FIGS. 5A and 5B: Detailed statistics of the two major loci linked to high ethanol tolerance. The tables show for each marker in the two mapped major loci (FIG. 5A: Chromosome V, FIG. 5B: chromosome XIV) the position of the marker, the number of segregants in which the marker was scored, the association percentage and the P value. The association percentage represents the percentage of segregants with VR1-5B inheritance, i.e., the nucleotide from VR1-5B. The markers with the strongest link are shown in bold.
Figure 5B:
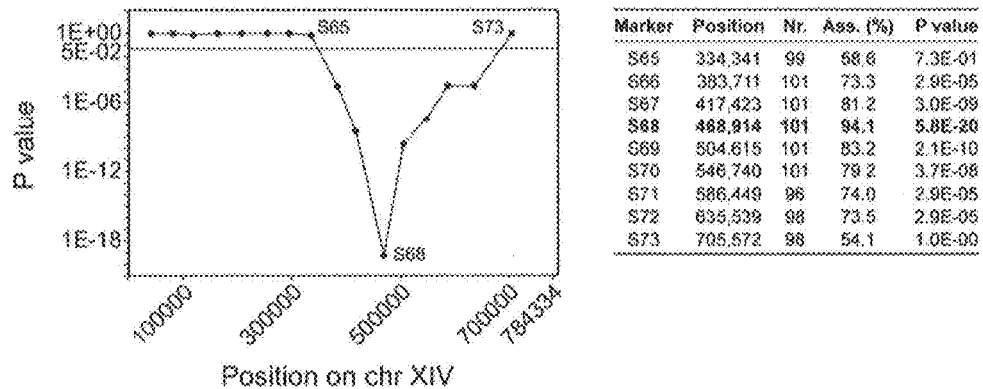

On the other hand, three loci showed a strong deviation from 50% inheritance, containing SNPs with a frequency of less than 20% or higher than 80% in the center of the locus. The loci were located on chromosomes V, X and XIV. The significance of the deviation in SNP nucleotide frequency could be confirmed by scoring a single SNP from the center of each locus in at least 96 individual highly ethanol tolerant segregants by PCR (Table 1). The QTLs on chromosome V (QTL1) and chromosome XIV (QTL3) showed the strongest link, with respectively 92.8% and 94.1% of the highly ethanol tolerant segregants harbouring the nucleotide from VR1-5B. The locus on chromosome X (QTL2) showed a much weaker link, with only 72.9% of the segregants showing VR1-5B inheritance. Scoring the same SNPs in an unselected pool of at least 80 segregants resulted in an association percentage of 50.0%, which is consistent with random segregation of the QTLs in an unselected pool of segregants. The joint effect of the three QTLs on high ethanol tolerance was examined by determining the appearance of each of the eight combinations in 85 highly ethanol tolerant segregants (Table 2). The combination between the VR1-5B-derived alleles from QTL1 and QTL3 was most prevalent in the segregants. Taken together, 88.2% of the highly ethanol tolerant segregants carried the VR1-5B-derived alleles from QTL1 and QTL3, indicating that inheriting both alleles is strongly advantageous for high ethanol tolerance. These results revealed that the VR1-5B-derived alleles from QTL1 and QTL3 are the major contributors to the high ethanol tolerance phenotype and that QTL2 is less important. The three identified QTLs were confirmed by whole-genome sequence analysis of DNA extracted from Pool 2 (17% ethanol) (FIG. 3). These data also revealed significant deviations from 50% inheritance at several other loci, which appear to represent minor loci determining high ethanol tolerance (FIG. 4). For example, a locus on chromosome II and on chromosome XV did not show a clear deviation from random segregation in the pool of segregants tolerant to 16% ethanol, whereas a clear deviation was observed in the pool of segregants tolerant to 17% ethanol (FIG. 2B). The boundaries of the two major loci (QTL1 and QTL3) identified in both pools by pooled-segregant whole genome sequence analysis were determined by scoring selected SNP markers in the region of the locus for at least 68 individual segregants that composed Pool 1 (16% ethanol) by PCR. We calculated the P value for each SNP using an exact binomial test with a confidence level of 95% and correction for multiple testing by a false discovery rate (FDR) control according to Benjamini-Yekutieli (2005). The P values were plotted over the length of the chromosome for each identified locus (FIGS. 5A and 5B).

Figure 6A:
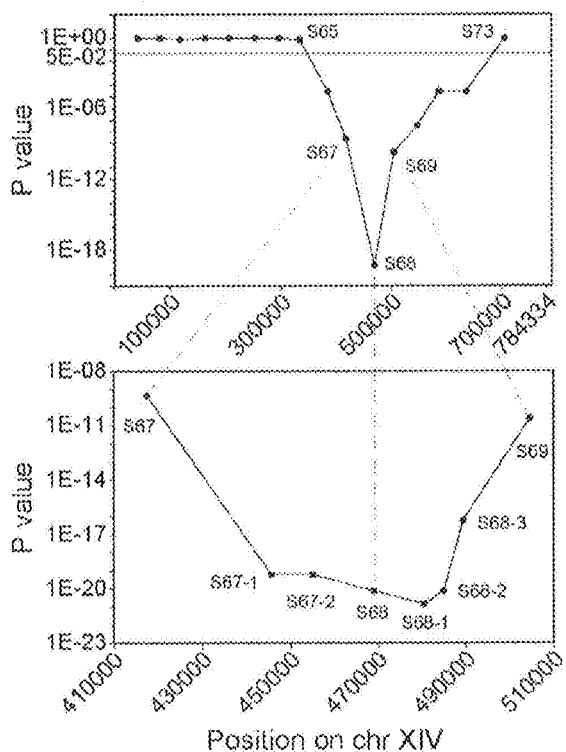
Figure 6B:
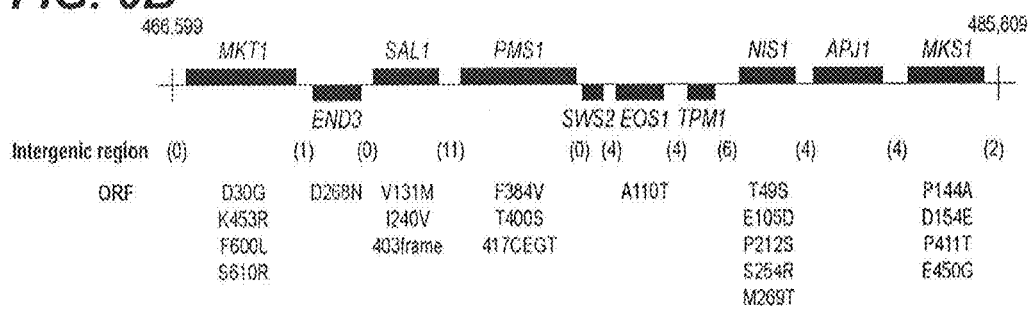
Figure 7C:
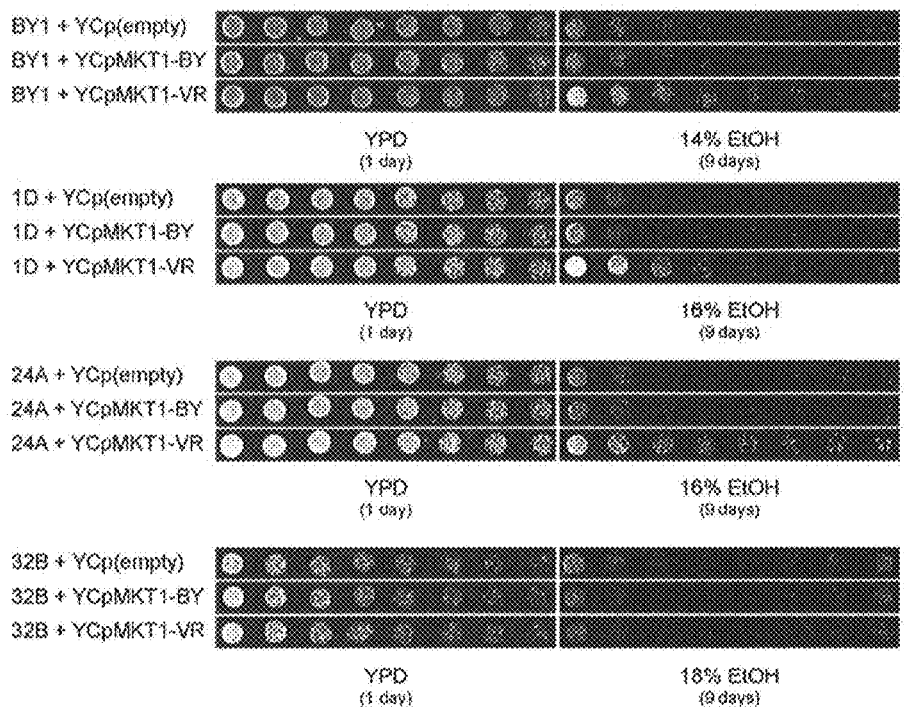

Example 3: Genetic Dissection of QTL3 Reveals Two Positive and One Negative Genetic Element The 370 kb QTL3 was fine-mapped using selected SNPs to reduce the size of the interval to a practical number of candidate genes for further functional analysis. The P values for eight SNP markers (S67, S67-1, S67-2, S68, S68-1, S68-2, S68-3, S69) defined a smaller locus of 16 kb between markers S68 and S68-2, which had the strongest link (FIG. 6A). The locus contained ten annotated genes (FIG. 6B). Sanger sequence analysis of this region was performed to detect all nucleotide polymorphisms between VR1-5B and BY4741 (FIG. 6B). We observed that VR1-5B and BY4741 were highly divergent with a polymorphism on average every 167 bp. All genes except TPM1 had at least one polymorphism in their ORF, being silent mutations for the genes APJ1 and SWS2 and missense mutations in the other seven genes. In addition, all genes had at least one polymorphism in their putative promoter and/or terminator. Given the difficulty to predict the effect of both coding and non-coding polymorphisms on phenotypes (Tabor et al., 2002), the sequence data could not be used to exclude genes from further functional analysis. Reciprocal hemizygosity analysis (RHA) was applied to identify the causative genes in the locus. RHA allows analyzing whether the two parental alleles have a different contribution to the phenotype in an otherwise uniform genetic background (Steinmetz et al., 2002). For nine genes, two heterozygous strains were constructed in the VR1-5B/BY4741 hybrid background that only differed genetically in the candidate gene, i.e., they carried either one copy of the VR1-5B or the BY4741 allele while the other copy of the gene was deleted (FIG. 6C). Comparing the ethanol tolerance of each pair of heterozygous strains revealed a difference in the phenotypic contribution between the parental alleles of MKT1, SWS2 and APJ1. The presence of the VR1-5B allele of the MKT1 and APJ1 gene resulted in higher ethanol tolerance compared to the BY4741 allele. For SWS2 the opposite was true, as the BY4741 allele was advantageous over the VR1-5B allele. One potential complication with RHA is that the hybrid diploid background used in the assay is different from the haploid segregants background used in the QTL mapping experiment. For this reason, we determined the deletion phenotypes of MKT1, SWS2 and APJ1 in the VR1-5B and BY4741 haploid strains. In the BY4741 background (which has a much lower ethanol tolerance), the MKT1Δ strain showed only a minor growth reduction while the APJ1Δ strain grew equally well as the wild type strain on 10% ethanol (FIG. 7A). Similar results were obtained on 12%, 14%, 15% and 16% ethanol (FIG. 7A). In contrast, deletion of SWS2 resulted in complete loss of growth on all ethanol levels (FIG. 7A). These results are in agreement with those of the screening of the BY deletion strain collection that only observed an ethanol sensitive growth phenotype for the sws2Δ strain. In the VR1-5B background (which has a much higher ethanol tolerance), deletion of SWS2 but also of MKT1, caused a severe growth defect on 10%, 12%, 14%, 15%, 16%, 17%, 18% and 19% ethanol (FIG. 7B). Interestingly, deletion of APJ1 had no effect for growth on 10% ethanol, but caused a clear growth improvement on 12%, 14%, 15% and 16% ethanol (FIG. 7A). Similar results were obtained for deletion of APB in the VR1-5B background, but the positive effect on the higher ethanol levels was smaller than in the BY4741 background (FIG. 7B). The improvement of ethanol tolerance by deletion of APJ1 indicates that the APJ1 gene product negatively affects ethanol tolerance. When this is combined with the result of the RHA analysis, it suggests that it suggests that the beneficial effect on ethanol tolerance of the APJ1-VR allele is due to lower expression compared to that of the APJ1-BY allele. The relevance of MKT1 for high ethanol tolerance was confirmed by expressing both parental alleles in BY4741 and in segregants from VR1-5B/BY4741 that hold the BY4741-derived allele of MKT1. Expression of MKT1-VR in contrast to MKT1-BY resulted in higher ethanol tolerance in BY4741 and two out of the three segregants (FIG. 7C). This confirmed the result from RHA suggesting that MKT1-VR is advantageous for high ethanol tolerance. On the other hand, as we did not observe an effect in all segregants, it seems that MKT1 alone is not sufficient to enhance ethanol tolerance. Comparing ethanol tolerance in the strains BY4741 and BY4741mkt1Δ confirmed that MKT1-BY is a loss-of-function allele, since no difference in ethanol tolerance was observed (FIG. 7C). In contrast, deletion of MKT1 in VR1-5B lowered ethanol tolerance (FIG. 7C), which confirms that a loss-of function mutation in MKT1 decreases ethanol tolerance.

Figure 8:
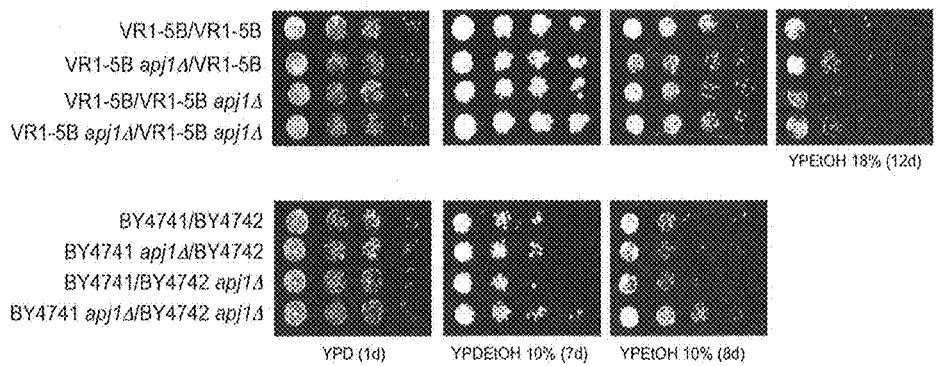
FIG. 8: Ethanol tolerance of diploid single and double APJ1 deletion parent strains. The ethanol tolerance of diploid single and double APJ1 deletion strains was determined on YP medium with 10% ethanol (after 7 and 8 days) and 18% ethanol (after 12 days) or with glucose (after 1 day) as control.

Also the single and double deletion of APJ1 in diploid strains improved ethanol tolerance. This was observed with the diploid VR1-B/VR1-B single and double APJ1 deletion strains and with the diploid BY4741/BY4741 double APJ1 deletion strain (FIG. 8).

Figure 9:
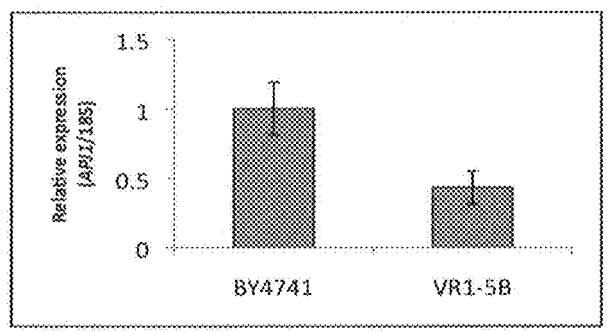
FIG. 9: Expression of APJ1 in BY4741 and VR1-5B strains during the beginning of the fermentation. Determination of APJ1 expression by Real-time PCR in BY4741 and VR1-5B strains during the beginning of the fermentation showed a higher expression level in the BY4741 strain (normalized to 1.0±0.19) compared to the VR1-5B strain (0.43±0.12). This agrees with the conclusion that Apj1p is negative for ethanol tolerance and that the APJ1 allele of VR1-5B is superior because of its lower expression.

The role of APJ1 is further confirmed by analysis of APJ1 expression in BY4741 and VR1-5B, using real time PCR (FIG. 9). VR1-5B shows a lower APJ1 expression and a higher ethanol resistance, supporting the idea that a high APJ1 expression is negative for ethanol tolerance.

Figure 10:
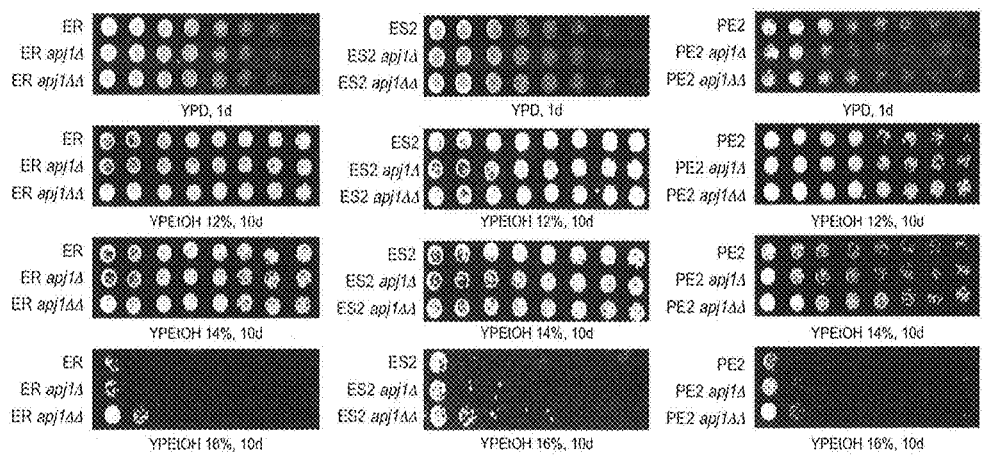
FIG. 10: Ethanol tolerance of industrial yeast strains with single and double APJ1 deletion. Ethanol tolerance of industrial yeast strains, Ethanol red (ER), ES2 and PE2, and its single and double APJ1 deletion strains was determined by scoring growth of twofold dilutions on nutrient plates with different ethanol concentrations (12%, 14% and 16%). Industrial strains with double APJ1 deletion showed a higher ethanol tolerance than the control strains on YP plates with 16% ethanol.

Example 4: Deletion of APJ1 Improves Ethanol Tolerance in Industrial Yeast Strains Single and double APJ1 deletion mutants were made from the diploid industrial yeast strains Ethanol red (ER), ES2 and PE2. The ethanol tolerance of the parental strains and of the single and double deletion mutants was scored by growth on YP plates with increasing ethanol concentration (10 days incubation, 12%, 14%, and 16% ethanol). Growth on YPD after 1 day incubation was used as control. The results are shown in FIG. 10. No difference in growth could be noticed for the control; all double mutants scored clearly better in ethanol tolerance.

Figure 11A:
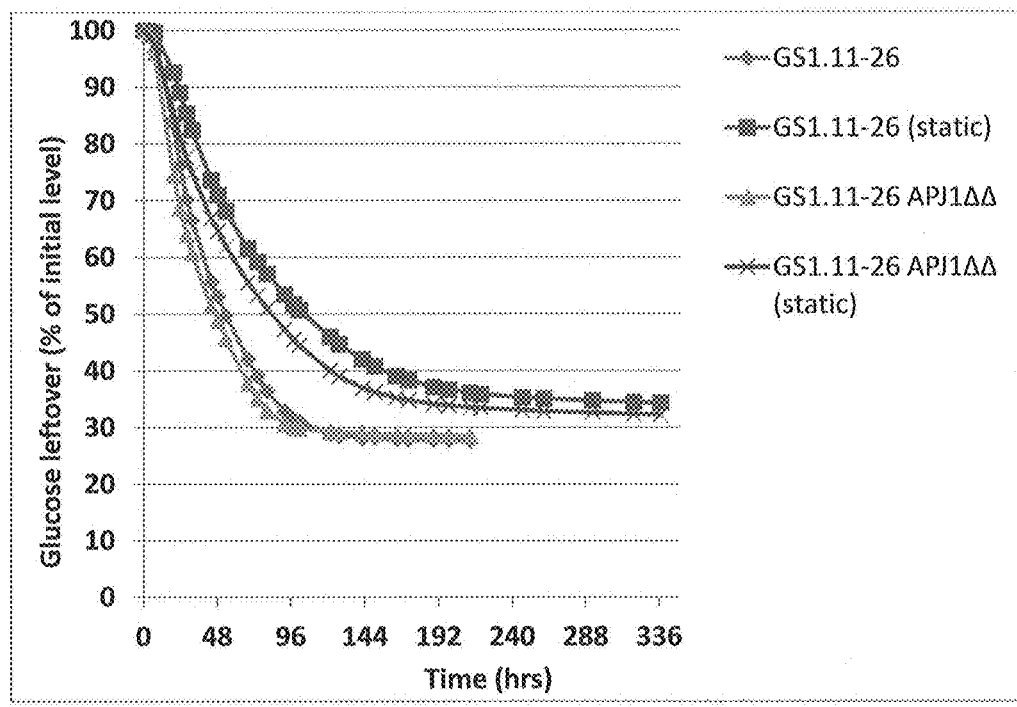
FIGS. 11A-11C: Comparison of fermentation performance in an industrial xylose utilizing strain with wild type APJ1 and the same strain deleted for APJ1 in both alleles. Fermentation was performed in YP+35% (w/v) glucose, in continuous stirring or static condition at 30° C. Values for stirring fermentations are average of duplicate experiments. Fermentation tubes were weighed every few hours and the amount of glucose leftover was inferred from the weight loss due to CO2 release.
Figure 11B:
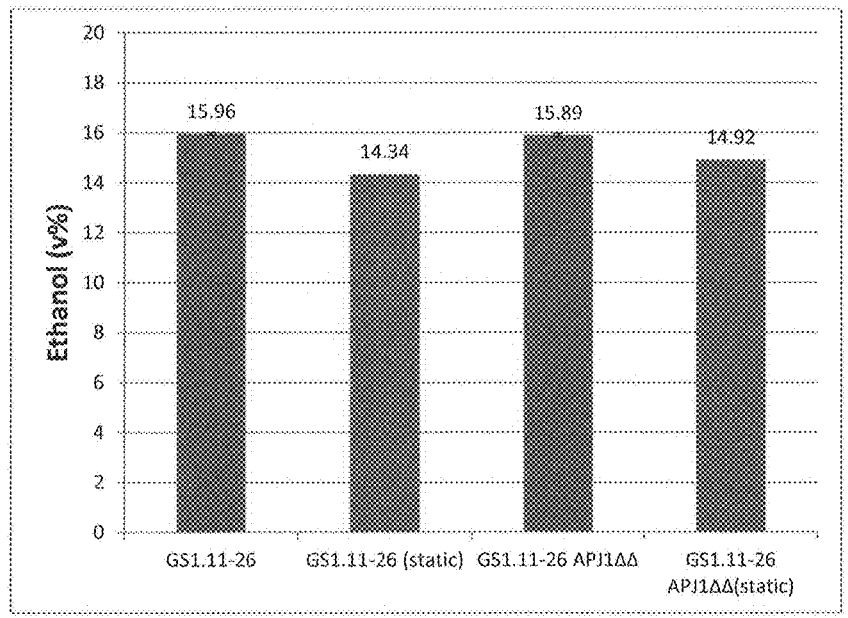
Figure 11C:
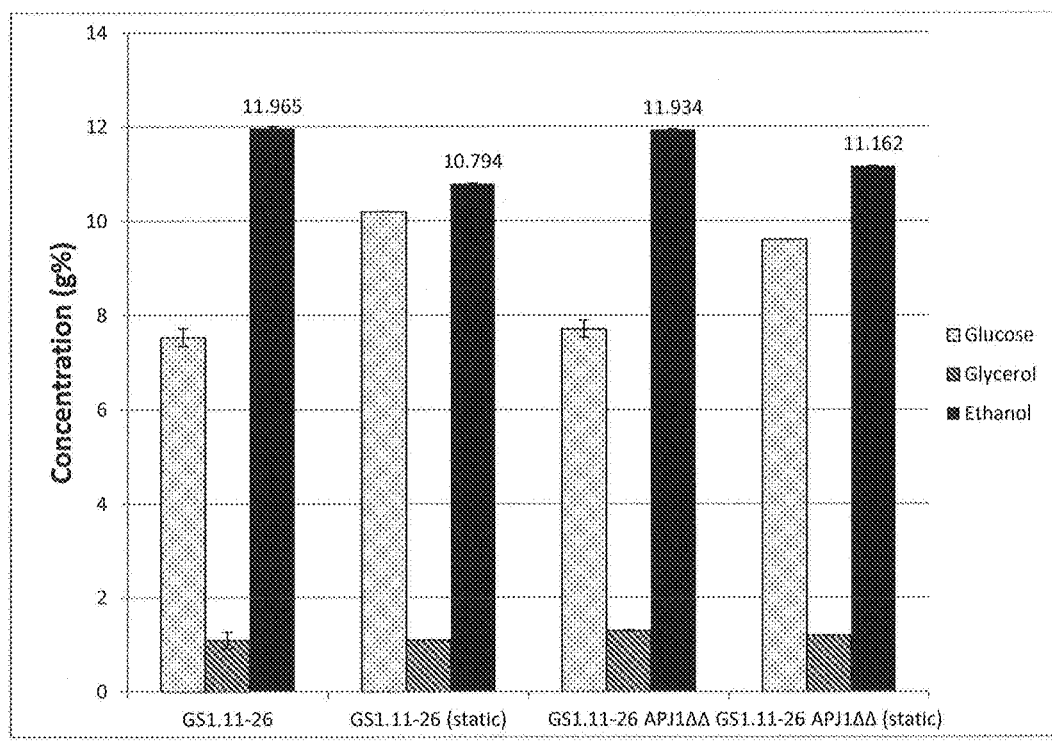

The ethanol tolerance inducing effect of the APJ1 deletion was further confirmed in high gravity fermentation. Both APJ1 alleles were deleted in the xylose utilizing ER derivative GS1.11-26 strain. The resulting double deletion strain was used in static and stirred high gravity fermentation in a YP medium comprising 35% glucose. The results are summarized in FIGS. 11A-11C. The double mutants were faster fermenting both in static and in stirred conditions. No clear difference in final ethanol production and glucose consumption could be seen in stirred conditions, but the double deletion mutant performed clearly better (higher ethanol production and glucose consumption at the end of the fermentation).

TABLE 1

Statistical confirmation of the significance of the three identified QTLs.

| Name | Position of SNP | Number | SNP frequency | P value |
|---|---|---|---|---|
| QTL1 | chr V; 122,599 | 125 | 92.8% | <<1.0E−09 |
| QTL2 | chr X; 659,775 | 96 | 72.9% | 8.1E−06 |
| QTL3 | chr XIV; 468,914 | 101 | 94.1% | <<1.0E−09 |

An SNP in the middle of each QTL was scored in at least 96 individual highly ethanol tolerant segregants by PCR ming specific primers for the two alleles. The P values were calculated with a confidence level of 95%.

TABLE 2

Appearance of each QTL combination in highly ethanol tolerant segregants.

| Combination | | | Frequency | Frequency (%) |
|---|---|---|---|---|
| qtl1 | qtl2 | qtl3 | 0/85 | 0.0% |
| qtl1 | qtl2 | QTL3 | 0/85 | 0.0% |
| qtl1 | QTL2 | qtl3 | 0/85 | 0.0% |
| QTL1 | qtl2 | qtl3 | 1/85 | 1.2% |
| qtl1 | QTL2 | QTL3 | 6/85 | 7.1% |
| QTL1 | QTL2 | qtl3 | 3/85 | 3.5% |
| QTL1 | qtl2 | QTL3 | 25/85 | 29.4% |
| QTL1 | QTL2 | QTL3 | 50/85 | 58.8% |

The origin (VR1-5B or BY) of a QTL in each of 85 highly ethanol tolerant segregants was derived from the genotype of an SNP marker in the middle of the QTL. The QTLs originating from BY are represented by small letters, while the QTLs originating from VR1-5B are represented by bold capital letters.

TABLE 3

SEQ ID NO: 1

```
  1  maikslesfl ferglvgsya iealnnctlg idvnhyvsrl ltnkreqyld aiggfptslk 61  mylesdlkif kdfnitpifv fnggltynql easghftaas asasissttt sssgtnattr 121  sntesvllqr srgwtqwnnl issnqnsyid qpiqpqepfr hnttidskay qndliayfie 181  hgymyqvapy sswfqlayll nsayidaiyg ptdclmldcv drfilgmefp nkefrfidrs 241  rvmkdlgcth eefidiamav gndlqpttlp plqiypvpql fdialemvln tgtnfyayql 301  sttlqndske niqnyqrgis alrympvlkd tgkvelfvqe ivvseedsek nnkdgkksnl 361  sspssasssa spattvtkna sekltyekss tkevrkprdi pndvhdfigq mlpheyyfyr 421  siglvtgklf daivtgvype epplgggsst syrklvsksv eifknkeinl ltqpinryyq 481  ikqikqvkwy aanepttltn rmspsmfeti nhlivktets dekefsisef ittingssnm 541  akdfisekvi fpnsvpiesk lnspfnllst nflrllvlle fftfdfkekl leptrwgevf 601  lklnelnids kyhesviifl vflkcdvlkl deevqppaps alsqatlrsy peeslyvlli 661  trvltlfqvd qkpsnyhgpi dkktlifrdh lsfikenlne lfeavlissl tsgefnrlsl 721  dnfgwarkiv rylpfkldsp ntimammwef flqkylhngn akndalslva tefntykstp 781  nldeqfvesh rflleiskvm qelnaaklid envfklftka veftttalss
```

REFERENCES

Altschul, S. F., T. L. Madden, A. A. Schäffer et al., *Nucleic Acids Research* 25, 3389 (1997).

Altschul, S. F., J. C. Wootton, E. M. Gertz et al., *FEBS J* 272, 5101 (2005).

Arnold, C. N., Y. Xia, P. Lin et al., *Genetics* 187, 633 (2011).

Benjamini, Y. and D. Yekutieli, *Genetics* 171 (2), 783 (2005).

Birkeland, S. R., N. Jin, A. C. Ozdemir et al., *Genetics* 186 (4), 1127 (2010).

Brachmann, C. B., A. Davies, G. J. Cost et al., *Yeast* 14 (2), 115 (1998).

Brem, R. B., G. Yvert, R. Clinton et al., *Science* 296 (5568), 752 (2002).

Cherry, J. C., C. Ball, S. Weng et al., *Nature* 387 (6632 Suppl), 67 (1997).

D'Amore, T. and G. G. Stewart, *Enzyme and Microbial Technology* 9, 322 (1987).

Del Sal, G., G. Manfioletti, and C. Schneider, *Nucleic Acids Res* 16, 9878 (1988).

Deutschbauer A. M. and R. W. Davis, *Nat Genet* 37 (12), 1333 (2005).

Ding, J., X. Huang, L. Zhang et al., *Appl Microbiol Biotechnol* 85 (2), 253 (2009).

Fujita, K., A. Matsuyama, Y. Kobayashi et al., *FEMS Yeast Res* 6 (5), 744 (2006).

Giaever, G., A. M. Chu, L. Ni et al., *Nature* 418 (6896), 387 (2002).

Gietz, R. D., R. H. Schiestl, A. R. Willems et al., *Yeast* 11 (4), 355 (1995).

Gietz, R. D. and A. Sugino, *Gene* 74 (2), 527 (1988).

Hoffman, C. S. and F. Winston, *Gene* 57 (2-3), 267 (1987).

Hu, X. H., M. H. Wang, T. Tan et al., *Genetics* 175 (3), 1479 (2007).

Huxley, C., E. D. Green, and I. Dunham, *Trends Genet* 6 (8), 236 (1990).

Johnston, J. R., *Molecular genetics of yeast: a practical approach*. (New York, 1994).

Lewis, J. A., I. M. Elkon, M. A. McGee et al., *Genetics* 186 (4), 1197 (2010).

Lister, R., B. D. Gregory, and J. R. Ecker, *Curr Opin Plant Biol* 12 (2), 107 (2009).

Marullo, P., M. Aigle, M. Bely et al., *FEMS Yeast Res* 7 (6), 941 (2007).

Michelmore, R. W., I. Paran, and R. V. Kesseli, *Proc Natl Acad Sci USA* 88 (21), 9828 (1991).

Nogami, S., Y. Ohya, and G. Yvert, *PLoS Genet* 3 (2), e31 (2007).

Perlstein, E. O., D. M. Ruderfer, D. C. Roberts et al., *Nat Genet* 39 (4), 496 (2007). Ruppert, D., M. P. Wand, and R. J. Carroll, *Semiparametric regression.* (Cambridge University Press, New York, 2003).
Sambrook, J., E. F. Fritsch, and T. Maniatis, edited by Cold Spring Harbor Laboratory Press (Cold Spring Harbor, N.Y., 1989).
Schneeberger, K., S. Ossowski, C. Lanz et al., *Nat Methods* 6 (8), 550 (2009).
Segrè, A. V., A. W. Murray, and J. Y. Leu, *PLoS Biol* 4 (8), e256 (2006).
Sherman, F. and J. Hicks, *Methods Enzymol* 194, 21 (1991).
Steinmetz, L. H., H. Sinha, D. R. Richards et al., *Nature* 416 (6878), 326 (2002).
Tabor, H. K., N. J. Risch, and R. M. Myers, *Nat Rev Genet* 3 (5), 391 (2002).
Teixeira, M. C., L. R. Raposo, N. P. Mira et al., *Appl Environ Microbiol* 75 (18), 5761 (2009).
van Voorst, F., J. Houghton-Larsen, L. Jonson et al., *Yeast* 23 (5), 351 (2006).
Wach, A., A. Brachat, R. Pohlmann et al., *Yeast* 10 (13), 1793 (1994).
Winzeler, E. A., D. R. Richards, A. R. Conway et al., *Science* 281 (5380), 1194 (1998).
Winzeler, E. A., D. D. Shoemaker, A. Astromoff et al., *Science* 285 (5429), 901 (1999).
Yoshikawa, K., T. Tanaka, C. Furusawa et al., *FEMS Yeast Res* 9 (1), 32 (2009).

What is claimed is:

1. An ethanol tolerant yeast comprising:
    a mutant MKT1 allele; and
    an overexpressed wild-type yeast SWS2 allele,
    wherein said mutant MKT1 encodes a protein consisting of an amino acid residue substitution of a glycine at a position corresponding to position 30 and an arginine at a position corresponding to position 453 of the amino acid sequence set forth in SEQ ID NO: 1; and wherein said ethanol tolerant yeast has a higher ethanol tolerance than a yeast without said mutant MKT1 allele and said overexpressed wild-type SWS2 allele.

2. The ethanol tolerant yeast of claim 1, wherein said yeast is a diploid, a polyploid, or an aneuploid strain and at least one copy of the MKT1 gene is said mutant MKT1 allele.

3. The ethanol tolerant yeast of claim 1, wherein said yeast is selected from the group consisting of *Saccharomyces*, *Zygosaccharomyces*, and *Brettanomyces*.

4. The ethanol tolerant yeast of claim 3, wherein said yeast is a *Saccharomyces cerevisiae*.

5. The ethanol tolerant yeast of claim 4, wherein said mutant MKT1 allele encodes a protein comprising the amino acid sequence of SEQ ID NO: 1.

6. The ethanol tolerant yeast of claim 4, wherein said wild-type yeast SWS2 allele encodes a protein comprising the amino acid sequence of SEQ ID NO: 4.

7. The ethanol tolerant yeast of claim 5, wherein said wild-type yeast SWS2 allele encodes a protein comprising the amino acid sequence of SEQ ID NO: 4.

8. The ethanol tolerant yeast of claim 2, wherein said yeast is selected from the group consisting of *Saccharomyces, Zygosaccharomyces*, and *Brettanomyces*.

9. The ethanol tolerant yeast of claim 8, wherein said yeast is a *Saccharomyces cerevisiae*.

10. The ethanol tolerant yeast of claim 9, wherein said mutant MKT1 allele encodes a protein comprising the amino acid sequence of SEQ ID NO: 1.

11. The ethanol tolerant yeast of claim 9, wherein said wild-type yeast SWS2 allele encodes a protein comprising the amino acid sequence of SEQ ID NO: 4.

12. The ethanol tolerant yeast of claim 10, wherein said wild-type yeast SWS2 allele encodes a protein comprising the amino acid sequence of SEQ ID NO: 4.

13. The ethanol tolerant yeast of claim 1, further comprising an inactivated yeast APJ1 allele.

14. The ethanol tolerant yeast of claim 2, further comprising an inactivated yeast APJ1 allele.

15. The ethanol tolerant yeast of claim 3, further comprising an inactivated yeast APJ1 allele.

16. The ethanol tolerant yeast of claim 4, further comprising an inactivated yeast APJ1 allele.

17. The ethanol tolerant yeast of claim 5, further comprising an inactivated yeast APJ1 allele.

18. The ethanol tolerant yeast of claim 6, further comprising an inactivated yeast APJ1 allele.

19. The ethanol tolerant yeast of claim 1, wherein said yeast is able to grow on plates with at least 14% ethanol.

20. A process for producing ethanol comprising culturing the ethanol tolerant yeast under conditions to produce ethanol.

* * * * *

SEQUENCE LISTING

```
<160> NUMBER OF SEQ ID NOS: 8

<210> SEQ ID NO 1
<211> LENGTH: 830
<212> TYPE: PRT
<213> ORGANISM: Saccharomyces cerevisiae

<400> SEQUENCE: 1

Met Ala Ile Lys Ser Leu Glu Ser Phe Leu Phe Glu Arg Gly Leu Val
1               5                   10                  15

Gly Ser Tyr Ala Ile Glu Ala Leu Asn Asn Cys Thr Leu Gly Ile Asp
            20                  25                  30

Val Asn His Tyr Val Ser Arg Leu Leu Thr Asn Lys Arg Glu Gln Tyr
        35                  40                  45

Leu Asp Ala Ile Gly Gly Phe Pro Thr Ser Leu Lys Met Tyr Leu Glu
    50                  55                  60

Ser Asp Leu Lys Ile Phe Lys Asp Phe Asn Ile Thr Pro Ile Phe Val
65                  70                  75                  80

Phe Asn Gly Gly Leu Thr Tyr Asn Gln Leu Glu Ala Ser Gly His Phe
                85                  90                  95

Thr Ala Ala Ser Ala Ser Ala Ser Ile Ser Ser Thr Thr Thr Ser Ser
            100                 105                 110

Ser Gly Thr Asn Ala Thr Thr Arg Ser Asn Thr Glu Ser Val Leu Leu
        115                 120                 125

Gln Arg Ser Arg Gly Trp Thr Gln Trp Asn Asn Leu Ile Ser Ser Asn
    130                 135                 140

Gln Asn Ser Tyr Ile Asp Gln Pro Ile Gln Pro Gln Glu Pro Phe Arg
145                 150                 155                 160

His Asn Thr Thr Ile Asp Ser Lys Ala Tyr Gln Asn Asp Leu Ile Ala
                165                 170                 175

Tyr Phe Ile Glu His Gly Tyr Met Tyr Gln Val Ala Pro Tyr Ser Ser
            180                 185                 190

Trp Phe Gln Leu Ala Tyr Leu Leu Asn Ser Ala Tyr Ile Asp Ala Ile
        195                 200                 205

Tyr Gly Pro Thr Asp Cys Leu Met Leu Asp Cys Val Asp Arg Phe Ile
    210                 215                 220

Leu Gly Met Glu Phe Pro Asn Lys Glu Phe Arg Phe Ile Asp Arg Ser
225                 230                 235                 240

Arg Val Met Lys Asp Leu Gly Cys Thr His Glu Glu Phe Ile Asp Ile
                245                 250                 255

Ala Met Ala Val Gly Asn Asp Leu Gln Pro Thr Thr Leu Pro Pro Leu
            260                 265                 270
```

```
Gln Ile Tyr Pro Val Pro Gln Leu Phe Asp Ile Ala Leu Glu Met Val
            275                 280                 285
Leu Asn Thr Gly Thr Asn Phe Tyr Ala Tyr Gln Leu Ser Thr Thr Leu
    290                 295                 300
Gln Asn Asp Ser Lys Glu Asn Ile Gln Asn Tyr Gln Arg Gly Ile Ser
305                 310                 315                 320
Ala Leu Arg Tyr Met Pro Val Leu Lys Asp Thr Gly Lys Val Glu Leu
                325                 330                 335
Phe Val Gln Glu Ile Val Val Ser Glu Asp Ser Glu Lys Asn Asn
            340                 345                 350
Lys Asp Gly Lys Lys Ser Asn Leu Ser Ser Pro Ser Ala Ser Ser
        355                 360                 365
Ser Ala Ser Pro Ala Thr Thr Val Thr Lys Asn Ala Ser Glu Lys Leu
    370                 375                 380
Thr Tyr Glu Lys Ser Ser Thr Lys Glu Val Arg Lys Pro Arg Asp Ile
385                 390                 395                 400
Pro Asn Asp Val His Asp Phe Ile Gly Gln Met Leu Pro His Glu Tyr
                405                 410                 415
Tyr Phe Tyr Arg Ser Ile Gly Leu Val Thr Gly Lys Leu Phe Asp Ala
            420                 425                 430
Ile Val Thr Gly Val Tyr Pro Glu Glu Pro Leu Gly Gly Gly Ser
        435                 440                 445
Ser Thr Ser Tyr Arg Lys Leu Val Ser Lys Ser Val Glu Ile Phe Lys
    450                 455                 460
Asn Lys Glu Ile Asn Leu Leu Thr Gln Pro Ile Asn Arg Tyr Tyr Gln
465                 470                 475                 480
Ile Lys Gln Ile Lys Gln Val Lys Trp Tyr Ala Ala Asn Glu Pro Thr
                485                 490                 495
Thr Leu Thr Asn Arg Met Ser Pro Ser Met Phe Glu Thr Ile Asn His
            500                 505                 510
Leu Ile Val Lys Thr Glu Thr Ser Asp Glu Lys Glu Phe Ser Ile Ser
        515                 520                 525
Glu Phe Ile Thr Thr Ile Asn Gly Ser Ser Asn Met Ala Lys Asp Phe
530                 535                 540
Ile Ser Glu Lys Val Ile Phe Pro Asn Ser Val Pro Ile Glu Ser Lys
545                 550                 555                 560
Leu Asn Ser Pro Phe Asn Leu Ser Thr Asn Phe Leu Arg Leu Leu
                565                 570                 575
Val Leu Leu Glu Phe Phe Thr Phe Asp Phe Lys Glu Lys Leu Leu Glu
            580                 585                 590
Pro Thr Arg Trp Gly Glu Val Phe Leu Lys Leu Asn Glu Leu Asn Ile
        595                 600                 605
Asp Ser Lys Tyr His Glu Ser Val Ile Ile Phe Leu Val Phe Leu Lys
    610                 615                 620
Cys Asp Val Leu Lys Leu Asp Glu Glu Val Gln Pro Ala Pro Ser
625                 630                 635                 640
Ala Leu Ser Gln Ala Thr Leu Arg Ser Tyr Pro Glu Glu Ser Leu Tyr
                645                 650                 655
Val Leu Leu Ile Thr Arg Val Leu Thr Leu Phe Gln Val Asp Gln Lys
            660                 665                 670
Pro Ser Asn Tyr His Gly Pro Ile Asp Lys Lys Thr Leu Ile Phe Arg
        675                 680                 685
Asp His Leu Ser Phe Ile Lys Glu Asn Leu Asn Glu Leu Phe Glu Ala
```

```
                690             695             700
Val Leu Ile Ser Ser Leu Thr Ser Gly Glu Phe Asn Arg Leu Ser Leu
705                 710                 715                 720

Asp Asn Phe Gly Trp Ala Arg Lys Ile Val Arg Tyr Leu Pro Phe Lys
                725                 730                 735

Leu Asp Ser Pro Asn Thr Ile Met Ala Met Met Trp Glu Phe Phe Leu
                740                 745                 750

Gln Lys Tyr Leu His Asn Gly Asn Ala Lys Asn Asp Ala Leu Ser Leu
                755                 760                 765

Val Ala Thr Glu Phe Asn Thr Tyr Lys Ser Thr Pro Asn Leu Asp Glu
770                 775                 780

Gln Phe Val Glu Ser His Arg Phe Leu Leu Glu Ile Ser Lys Val Met
785                 790                 795                 800

Gln Glu Leu Asn Ala Ala Lys Leu Ile Asp Glu Asn Val Phe Lys Leu
                805                 810                 815

Phe Thr Lys Ala Val Glu Phe Thr Thr Thr Ala Leu Ser Ser
                820                 825                 830

<210> SEQ ID NO 2
<211> LENGTH: 528
<212> TYPE: PRT
<213> ORGANISM: Saccharomyces cerevisiae

<400> SEQUENCE: 2

Met Gln Gln Asn Thr Ser Leu Tyr Asp Ser Leu Asn Val Thr Ala Ala
1               5                   10                  15

Ala Ser Thr Ser Glu Ile Lys Lys Ala Tyr Arg Asn Ala Ala Leu Lys
                20                  25                  30

Tyr His Pro Asp Lys Asn Asn His Thr Glu Glu Ser Lys Arg Lys Phe
            35                  40                  45

Gln Glu Ile Cys Gln Ala Tyr Glu Ile Leu Lys Asp Asn Arg Leu Arg
        50                  55                  60

Ala Leu Tyr Asp Gln Tyr Gly Thr Thr Asp Glu Val Leu Ile Gln Glu
65                  70                  75                  80

Gln Gln Ala Gln Ala Gln Arg Gln Gln Ala Gly Pro Phe Ser Ser Ser
                85                  90                  95

Ser Asn Phe Asp Thr Glu Ala Met Ser Phe Pro Asp Leu Ser Pro Gly
                100                 105                 110

Asp Leu Phe Ala Gln Phe Phe Asn Ser Ser Ala Thr Pro Ser Ser Asn
            115                 120                 125

Gly Ser Lys Ser Ser Phe Asn Phe Ser Phe Asn Asn Ser Ser Thr Pro
        130                 135                 140

Ser Phe Ser Phe Val Asn Gly Ser Gly Val Asn Asn Leu Tyr Ser Ser
145                 150                 155                 160

Ser Ala Lys Tyr Asn Ser Asn Asp Glu Asp His His Leu Asp Arg Gly
                165                 170                 175

Pro Asp Ile Lys His Asn Leu Lys Cys Thr Leu Lys Glu Leu Tyr Met
            180                 185                 190

Gly Lys Thr Ala Lys Leu Gly Leu Asn Arg Thr Arg Ile Cys Ser Val
        195                 200                 205

Cys Asp Gly His Gly Gly Leu Lys Lys Cys Thr Cys Lys Thr Cys Lys
    210                 215                 220

Gly Gln Gly Ile Gln Thr Gln Thr Arg Arg Met Gly Pro Leu Val Gln
225                 230                 235                 240
```

-continued

Ser Trp Ser Gln Thr Cys Ala Asp Cys Gly Gly Ala Gly Val Phe Val
            245                 250                 255

Lys Asn Lys Asp Ile Cys Gln Cys Gln Gly Leu Gly Phe Ile Lys
        260                 265                 270

Glu Arg Lys Ile Leu Gln Val Thr Val Gln Pro Gly Ser Cys His Asn
        275                 280                 285

Gln Leu Ile Val Leu Thr Gly Glu Gly Asp Glu Val Ile Ser Thr Lys
    290                 295                 300

Gly Gly Gly His Glu Lys Val Ile Pro Gly Asp Val Val Ile Thr Ile
305                 310                 315                 320

Leu Arg Leu Lys Asp Pro Asn Phe Gln Val Ile Asn Tyr Ser Asn Leu
                325                 330                 335

Ile Cys Lys Lys Cys Lys Ile Asp Phe Met Thr Ser Leu Cys Gly Gly
                340                 345                 350

Val Val Tyr Ile Glu Gly His Pro Ser Gly Lys Leu Ile Lys Leu Asp
            355                 360                 365

Ile Ile Pro Gly Glu Ile Leu Lys Pro Gly Cys Phe Lys Thr Val Glu
    370                 375                 380

Asp Met Gly Met Pro Lys Phe Ile Asn Gly Val Arg Ser Gly Phe Gly
385                 390                 395                 400

His Leu Tyr Val Lys Phe Asp Val Thr Tyr Pro Glu Arg Leu Glu Pro
                405                 410                 415

Glu Asn Ala Lys Lys Ile Gln Asn Ile Leu Ala Asn Asp Lys Tyr Ile
                420                 425                 430

Lys Ala Glu Arg Ser Thr Met Glu Thr Ala Asp Ser Asp Cys Tyr Cys
            435                 440                 445

Asp Leu Glu Lys Ser Tyr Asp Ser Val Glu Glu His Val Leu Ser Ser
450                 455                 460

Phe Glu Ala Pro Asn Leu Asn Asn Glu Val Ile Glu Asp Asp Leu
465                 470                 475                 480

Gly Asp Leu Ile Asn Glu Arg Asp Ser Arg Lys Arg Asn Asn Arg Arg
                485                 490                 495

Phe Asp Glu Ser Asn Ile Asn Asn Asn Glu Thr Lys Arg Asn Lys
            500                 505                 510

Tyr Ser Ser Pro Val Ser Gly Phe Tyr Asp His Asp Ile Asn Gly Tyr
            515                 520                 525

<210> SEQ ID NO 3
<211> LENGTH: 830
<212> TYPE: PRT
<213> ORGANISM: Saccharomyces cerevisiae

<400> SEQUENCE: 3

Met Ala Ile Lys Ser Leu Glu Ser Phe Leu Phe Glu Arg Gly Leu Val
1               5                   10                  15

Gly Ser Tyr Ala Ile Glu Ala Leu Asn Asn Cys Thr Leu Asp Ile Asp
            20                  25                  30

Val Asn His Tyr Val Ser Arg Leu Leu Thr Asn Lys Arg Glu Gln Tyr
        35                  40                  45

Leu Asp Ala Ile Gly Gly Phe Pro Thr Ser Leu Lys Met Tyr Leu Glu
    50                  55                  60

Ser Asp Leu Lys Ile Phe Lys Asp Phe Asn Ile Thr Pro Ile Phe Val
65                  70                  75                  80

Phe Asn Gly Gly Leu Thr Tyr Asn Gln Leu Glu Ala Ser Gly His Phe
                85                  90                  95

-continued

Thr Ala Ala Ser Ala Ser Ala Ser Ile Ser Ser Thr Thr Ser Ser
            100                 105                 110

Ser Gly Thr Asn Ala Thr Thr Arg Ser Asn Thr Glu Ser Val Leu Leu
            115                 120                 125

Gln Arg Ser Arg Gly Trp Thr Gln Trp Asn Asn Leu Ile Ser Ser Asn
130                 135                 140

Gln Asn Ser Tyr Ile Asp Gln Pro Ile Gln Pro Gln Glu Pro Phe Arg
145                 150                 155                 160

His Asn Thr Thr Ile Asp Ser Lys Ala Tyr Gln Asn Asp Leu Ile Ala
                165                 170                 175

Tyr Phe Ile Glu His Gly Tyr Met Tyr Gln Val Ala Pro Tyr Ser Ser
            180                 185                 190

Trp Phe Gln Leu Ala Tyr Leu Leu Asn Ser Ala Tyr Ile Asp Ala Ile
            195                 200                 205

Tyr Gly Pro Thr Asp Cys Leu Met Leu Asp Cys Val Asp Arg Phe Ile
            210                 215                 220

Leu Gly Met Glu Phe Pro Asn Lys Glu Phe Arg Phe Ile Asp Arg Ser
225                 230                 235                 240

Arg Val Met Lys Asp Leu Gly Cys Thr His Glu Glu Phe Ile Asp Ile
                245                 250                 255

Ala Met Ala Val Gly Asn Asp Leu Gln Pro Thr Thr Leu Pro Pro Leu
            260                 265                 270

Gln Ile Tyr Pro Val Pro Gln Leu Phe Asp Ile Ala Leu Glu Met Val
            275                 280                 285

Leu Asn Thr Gly Thr Asn Phe Tyr Ala Tyr Gln Leu Ser Thr Thr Leu
            290                 295                 300

Gln Asn Asp Ser Lys Glu Asn Ile Gln Asn Tyr Gln Arg Gly Ile Ser
305                 310                 315                 320

Ala Leu Arg Tyr Met Pro Val Leu Lys Asp Thr Gly Lys Val Glu Leu
                325                 330                 335

Phe Val Gln Glu Ile Val Val Ser Glu Glu Asp Ser Glu Lys Asn Asn
            340                 345                 350

Lys Asp Gly Lys Lys Ser Asn Leu Ser Ser Pro Ser Ser Ala Ser Ser
            355                 360                 365

Ser Ala Ser Pro Ala Thr Thr Val Thr Lys Asn Ala Ser Glu Lys Leu
            370                 375                 380

Thr Tyr Glu Lys Ser Ser Thr Lys Glu Val Arg Lys Pro Arg Asp Ile
385                 390                 395                 400

Pro Asn Asp Val His Asp Phe Ile Gly Gln Met Leu Pro His Glu Tyr
                405                 410                 415

Tyr Phe Tyr Arg Ser Ile Gly Leu Val Thr Gly Lys Leu Phe Asp Ala
            420                 425                 430

Ile Val Thr Gly Val Tyr Pro Glu Glu Pro Pro Leu Gly Gly Gly Ser
            435                 440                 445

Ser Thr Ser Tyr Lys Lys Leu Val Ser Lys Ser Val Glu Ile Phe Lys
            450                 455                 460

Asn Lys Glu Ile Asn Leu Leu Thr Gln Pro Ile Asn Arg Tyr Tyr Gln
465                 470                 475                 480

Ile Lys Gln Ile Lys Gln Val Lys Trp Tyr Ala Ala Asn Glu Pro Thr
                485                 490                 495

Thr Leu Thr Asn Arg Met Ser Pro Ser Met Phe Glu Thr Ile Asn His
            500                 505                 510

```
Leu Ile Val Lys Thr Glu Thr Ser Asp Glu Lys Glu Phe Ser Ile Ser
            515                 520                 525

Glu Phe Ile Thr Thr Ile Asn Gly Ser Ser Asn Met Ala Lys Asp Phe
        530                 535                 540

Ile Ser Glu Lys Val Ile Phe Pro Asn Ser Val Pro Ile Glu Ser Lys
545                 550                 555                 560

Leu Asn Ser Pro Phe Asn Leu Ser Thr Asn Phe Leu Arg Leu Leu
                565                 570                 575

Val Leu Leu Glu Phe Phe Thr Phe Asp Phe Lys Glu Lys Leu Leu Glu
            580                 585                 590

Pro Thr Arg Trp Gly Glu Val Phe Leu Lys Leu Asn Glu Leu Asn Ile
        595                 600                 605

Asp Ser Lys Tyr His Glu Ser Val Ile Ile Phe Leu Val Phe Leu Lys
        610                 615                 620

Cys Asp Val Leu Lys Leu Asp Glu Glu Val Gln Pro Pro Ala Pro Ser
625                 630                 635                 640

Ala Leu Ser Gln Ala Thr Leu Arg Ser Tyr Pro Glu Glu Ser Leu Tyr
            645                 650                 655

Val Leu Leu Ile Thr Arg Val Leu Thr Leu Phe Gln Val Asp Gln Lys
            660                 665                 670

Pro Ser Asn Tyr His Gly Pro Ile Asp Lys Lys Thr Leu Ile Phe Arg
        675                 680                 685

Asp His Leu Ser Phe Ile Lys Glu Asn Leu Asn Glu Leu Phe Glu Ala
        690                 695                 700

Val Leu Ile Ser Ser Leu Thr Ser Gly Glu Phe Asn Arg Leu Ser Leu
705                 710                 715                 720

Asp Asn Phe Gly Trp Ala Arg Lys Ile Val Arg Tyr Leu Pro Phe Lys
                725                 730                 735

Leu Asp Ser Pro Asn Thr Ile Met Ala Met Trp Glu Phe Phe Leu
                740                 745                 750

Gln Lys Tyr Leu His Asn Gly Asn Ala Lys Asn Asp Ala Leu Ser Leu
            755                 760                 765

Val Ala Thr Glu Phe Asn Thr Tyr Lys Ser Thr Pro Asn Leu Asp Glu
770                 775                 780

Gln Phe Val Glu Ser His Arg Phe Leu Leu Glu Ile Ser Lys Val Met
785                 790                 795                 800

Gln Glu Leu Asn Ala Ala Lys Leu Ile Asp Glu Asn Val Phe Lys Leu
            805                 810                 815

Phe Thr Lys Ala Val Gly Phe Thr Thr Thr Ala Leu Ser Ser
            820                 825                 830

<210> SEQ ID NO 4
<211> LENGTH: 143
<212> TYPE: PRT
<213> ORGANISM: Saccharomyces cerevisiae

<400> SEQUENCE: 4

Met Val Val His Ile Leu Gly Lys Gly Phe Lys Gly Lys Glu Val Ile
1               5                   10                  15

Lys Ile Ala Leu Ala Ser Lys Phe Tyr Gly Ile Gly Lys Thr Thr Ala
            20                  25                  30

Glu Lys Ile Cys Ser Lys Leu Gly Phe Tyr Pro Trp Met Arg Met His
        35                  40                  45

Gln Leu Ser Glu Pro Gln Ile Met Ser Ile Ala Ser Glu Leu Ser Thr
    50                  55                  60
```

```
Met Thr Ile Glu Gly Asp Ala Arg Ala Ile Val Lys Asp Asn Ile Ala
65                  70                  75                  80

Leu Lys Arg Lys Ile Gly Ser Tyr Ser Gly Met Arg His Thr Leu His
                85                  90                  95

Leu Pro Val Arg Gly Gln His Thr Arg Asn Asn Ala Lys Thr Ala Arg
            100                 105                 110

Lys Leu Asn Lys Ile Asp Arg Arg Gly Ile His Thr Phe Ser Gln Ala
        115                 120                 125

Lys Val Gln His Asn Pro Ser Leu Trp Ser Cys Ile Phe Gly Lys
    130                 135                 140

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
tgatgggcac ggtggtcta                                           19

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ttgaatacct tgccctttgc a                                        21

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
cacttcttag agggactatc ggtttc                                   26

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
cagaacgtct aagggcatca ca                                       22
```